US012590318B2

(12) United States Patent
Hall et al.

(10) Patent No.: US 12,590,318 B2
(45) Date of Patent: Mar. 31, 2026

(54) INSECT INHIBITORY PROTEINS

(71) Applicant: Monsanto Technology LLC, St. Louis, MO (US)

(72) Inventors: Erin L. Hall, Collinsville, IL (US); Arlene R. Howe, Clarkson Valley, MO (US); Brent A. O'Brien, St. Charles, MO (US); James K. Roberts, Chesterfield, MO (US); Francesca L. Stubbins, St. Louis, MO (US); Stephanie C. Waldheuser, Eureka, MO (US)

(73) Assignee: Monsanto Technology LLC, St. Louis, MO (US)

( * ) Notice: Subject to any disclaimer, the term of this patent is extended or adjusted under 35 U.S.C. 154(b) by 148 days.

(21) Appl. No.: 18/529,422

(22) Filed: Dec. 5, 2023

(65) Prior Publication Data

US 2024/0200092 A1 Jun. 20, 2024

Related U.S. Application Data

(60) Provisional application No. 63/386,432, filed on Dec. 7, 2022.

(51) Int. Cl.
| | |
|---|---|
| *C12N 15/82* | (2006.01) |
| *A01N 63/20* | (2020.01) |
| *A01N 63/50* | (2020.01) |
| *A01P 7/04* | (2006.01) |

(52) U.S. Cl.
CPC ......... *C12N 15/8286* (2013.01); *A01N 63/20* (2020.01); *A01N 63/50* (2020.01); *A01P 7/04* (2021.08); *C12N 15/8205* (2013.01)

(58) Field of Classification Search
None
See application file for complete search history.

(56) References Cited

U.S. PATENT DOCUMENTS

| | | | |
|---|---|---|---|
| 10,787,679 B2 * | 9/2020 | Parks ..................... | C07K 14/32 |
| 11,492,640 B2 | 11/2022 | Bowen et al. | |
| 2003/0226171 A1 | 12/2003 | Jansens et al. | |

| | | | |
|---|---|---|---|
| 2018/0066277 A1 | 3/2018 | Parks et al. | |
| 2020/0229445 A1 * | 7/2020 | Bowen ................. | C12Q 1/6895 |
| 2020/0370066 A1 | 11/2020 | Bowen et al. | |

FOREIGN PATENT DOCUMENTS

| | | |
|---|---|---|
| WO | 2022146874 | 7/2022 |

OTHER PUBLICATIONS

International Search Report and Written Opinion regarding International Application No. PCT/US2023/082423, mailed Apr. 2, 2024.
Alphey, et al. "Combining pest control and resistance management: synergy of engineered insects with Bt crops." Journal of Economic Entomology, 102: 717-732, (2009).
ISAAA. 2016. Global Status of Commercialized Biotech/GM Crops: 2016. ISAAA Brief No. 52. ISAAA: Ithaca, NY.
Jin, et al., "Engineered female-specific lethality for control of pest Lepidoptera." ACS Synthetic Biology, 2: 160-166, (2013).
Pacheco, et al., "Gene Editing and Genetic Control of Hemipteran Pests: Progress, Challenges and Perspectives", Frontiers in Bioengineering and Biotechnology, 10:1-26, (2022).
Zhou, et al., "Combining the high-dose/refuge strategy and self-limiting transgenic insects in resistance management—a test in experimental mesocosms." Evol Appl 11(5):727-738, (2018).
Matos. Invitation to Pay Additional Fees regarding International App. No. PCT/US23/82423, mailed Feb. 16, 2024.

* cited by examiner

*Primary Examiner* — Charles Logsdon
*Assistant Examiner* — Jessica Nicole Stockdale
(74) *Attorney, Agent, or Firm* — Dentons US LLP; David Lanzotti

(57) ABSTRACT

Pesticidal protein exhibiting toxic activity against Hemipteran and Lepidopteran pest species are disclosed, and include, but are not limited to, TIC11207 and TIC11304. DNA constructs are provided which contain a recombinant nucleic acid sequence encoding the disclosed pesticidal protein. Transgenic plants, plant cells, seed, and plant parts resistant to Hemipteran and Lepidopteran infestation are provided which contain recombinant nucleic acid sequences encoding the pesticidal proteins of the present invention. Methods for detecting the presence of the recombinant nucleic acid sequences or the protein of the present invention in a biological sample, and methods of controlling Hemipteran and Lepidopteran species pests using TIC11207 and TIC11304 pesticidal proteins are also provided.

17 Claims, 3 Drawing Sheets

Specification includes a Sequence Listing.

```
TIC11207  MSDSPGINISMVAAPTQAGCSIGAVGKMVKPIQDSDVPYFFPNGVVSAMQHHYPGYRIGG
TIC11304  MSDSPGINISMVAAPTPAGCSIGAVGKMVRPIQDSDVPYFFPNGVVSAMQHHYPGYNIGG
APG01463  MSDSPGINISMVAAPTQARCSVGATGKIVKQIEDSDIPYFFPNGVVSSAMQHHFPHNKIGG
          *  *****  ********  **  **  *  *****  ******  *  **  *

TIC11207  AWLHDPTPGAPYSDMFAYYKDWPGGPTPVTVIYKPVSARVVSMSPEAAYKYDQDFINDSS
TIC11304  AWLHDPTPGAPYSDMFAYYKDWPGGPTPVTVIYKPVSARVVSMSPEAAYKYDQDFINESS
APG01463  AWLHDPTPGAPYSNMFDYYKNWQGGPSPVTVVYKPVSAKIVSLTPEDAYKYDQEFINDSS
          ************  **  **  **  ***  ****  ****  *  **  *****  ****

TIC11207  VGATFNCSLTQSVTNSVSTTKTEGDSLKVGQKLTYGVEFLGSGVKGETSAEYTHTWGTSD
TIC11304  VGATFNCSLTQSVTNSVSTTKTEGDSLKVGQKLTYGVEFLGSGVKGETSAEYTHTWGTSD
APG01463  VPGTFNCSLTQSVTNSVSTTKTEGDSLKVGQKFGYGVEFLGTGAKGETSAEYQHSWGTSD
          *  *********************************  *****  *  ********  *  ****

TIC11207  TNTTTVTVGTASGISVFLEPGQKVTAELTASRSKLVVEVTYDVTLDGSVVFTTPNWDLGG
TIC11304  TNTTTVTVGTASGISVFLEPGQKVTAELTASRSKLVVEVTYDVTLDGSVVFTTPNWDLGG
APG01463  TNMTTVTVGTSTGLSVLLQPGQRVKAELSAAHSKLVVEVTYDVTLDGSVIYTFPNWDDG--
          **  ******  *  **  *  ***  *  ***  *  *****************  *  ****  *

TIC11207  HRDHWFWVGSLLDDANGGNPPNSSVGIRRTEQITLDFYANGVTRLLDNTGKVLLTVKDGH
TIC11304  HRDHWFWVGSLLDDANGGNPPNSSVGIRRTEQITLDFYANGVTRLLDNTGKVLLTVEGGR
APG01463  HRDHWFWAGSLLDDANGGNPPNSSVGIRRTEQITLDYYSNGVTRLLDINGNLLLTVEDGH
          *******  ***********************  ***  *  ******  *  *****  **

TIC11207  GRAEAKDEESLTLEALREAASQGA
TIC11304  GQAEAKDEKSFTLEALREAASLGA
APG01463  GRGEAKDGGPLTLEELRKQLR---
          *  *****  ******  *  *  *
```

FIG. 1

INSECT INHIBITORY PROTEINS

REFERENCE TO RELATED APPLICATIONS

This application claims the benefit of U.S. provisional application No. 63/386,432, filed Dec. 7, 2022, all herein incorporated by reference in their entirety.

INCORPORATION OF SEQUENCE LISTING

The file named "MONS571US_ST26_revised.xml" containing a computer-readable form of the Sequence Listing was created on Jun. 13, 2024. This file is 39,879 bytes (measured in MS-Windows®), filed contemporaneously by electronic submission (using the United States Patent Office Patent Center), and incorporated by reference in its entirety.

FIELD OF THE INVENTION

The invention generally relates to the field of insect inhibitory proteins. A novel class of toxin proteins are disclosed exhibiting insect inhibitory activity against agriculturally-relevant pests of crop plants and seeds, particularly Hemipteran species of insect pests. Plants, plant parts, seed, cells including plant and microbial cells, and vectors containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, cotton, vegetables, pearl millets, pigeon pea, peanut, potato, barley, oat, fruit trees, and the like has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these factors, environmentally sustainable improvements in technology, agricultural techniques, and pest management are vital tools to expand crop production on the increasingly limited amount of arable land available for farming.

Insects, particularly insects within the order of Hemiptera, are a major cause of damage to field crops, thereby decreasing crop yields over infested areas. Hemipteran pest species which negatively impact agriculture include, but are not limited to, Southern Green Stink Bug (*Nezara viridula*), Neotropical Brown Stink Bug (*Euschistus heros*), Brown Marmorated Stink Bug (*Halyomorpha halys*), Red-Shouldered Stink Bug (*Thyanta accerra*), Green Belly Stink Bug (*Dichelops melacanthus*), Western tarnished plant bug (*Lygus hesperus*), and Tarnished plant bug (*Lygus lineolaris*).

Historically, the intensive application of synthetic chemical insecticides was relied upon as the pest control agent in agriculture. Concerns for the environment and human health, in addition to emerging resistance issues and the fact that such pest control agents do not discriminate and target beneficial insects and other organisms as well, stimulated the research and development of biological pesticides specifically targeted to control the pests that create the crop loss.

This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus, Lysinibacillus sphaericus* ("Ls" formerly known as *Bacillus sphaericus*), *Pseudomonas* species, *Paenibacillus popilliae* and *Paenibacillus lentimorbus*. In addition, insecticidal toxins have also been identified from a variety of non-bacterial sources including ferns, arachnid venoms, and delivery in a diet of a pest of dsRNA targeting for suppression an essential gene has been identified as an effective pest management strategy.

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein(s).

The use of transgenic plants expressing insecticidal toxin proteins has been globally adapted. For example, in 2016, 23.1 million hectares were planted with transgenic crops expressing Bt toxins and 75.4 million hectares were planted with transgenic crops expressing Bt toxins stacked with herbicide tolerance traits (ISAAA. 2016. Global Status of Commercialized Biotech/GM Crops: 2016. ISAAA Brief No. 52. ISAAA: Ithaca, NY). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action or alternatively two or more different modes of toxic action (for example, a transgene encoding a dsRNA targeting an essential gene for suppression coupled with a transgene that encodes a peptide or protein toxin, both toxic to the same insect species) reduces the probability of resistance in any single target insect species. Additionally, use of self-limiting technologies such as those provided by Oxitec Ltd, when used together with the proteins of the present invention, should improve durability of the traits imparted to transgenic crops expressing proteins of the present invention (Zhou et al. 2018. Combining the high-dose/refuge strategy and self-limiting transgenic insects in resistance management—a test in experimental mesocosms. Evol Appl 11 (5): 727-738; Alphey et al. 2009. Combining pest control and resistance management: synergy of engineered insects with Bt crops. Journal of Economic Entomology, 102:717-732).

Thus, the inventors disclose herein novel proteins from *Paenarthrobacter nitroguajacolicus*, that exhibit insecticidal activity against target Hemipteran species, particularly Southern Green Stink Bug (*Nezara viridula*), Neotropical Brown Stink Bug (*Euschistus heros*), and Western tarnished plant bug (*Lygus hesperus*).

SUMMARY OF THE INVENTION

Disclosed herein are novel pesticidal proteins, TIC11207 and TIC11304, which are shown to exhibit inhibitory activity against one or more pests of crop plants. The TIC11207 and TIC11304 proteins can be used alone or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter operably linked to a polynucleotide segment encoding a pesticidal protein or pesticidal fragment thereof, wherein the pesticidal protein comprises the amino acid sequence of SEQ ID NOs: 2, 4, 12, 14, 17, or 19; or the pesticidal protein comprises an amino acid sequence having at least 80%, or 85%, or 90%, or 95%, or about 100% amino acid sequence identity to SEQ ID NOs: 2, 4, 12, 14, 17, or 19; or the polynucleotide segment hybridizes under stringent hybridization conditions to a polynucleotide having the nucleotide sequence of SEQ ID NOs: 1, 3, 5, 6, 7, 8, 9, 10, 11, 13, 15, 16, or 18. The recombinant nucleic acid molecule can comprise a sequence that functions to express the pesticidal protein in a plant, and which when expressed in a plant cell produces a pesticidally effective amount of pesticidal protein or a pesticidal fragment thereof.

In another embodiment of this application the recombinant nucleic acid molecule is present within a bacterial or plant host cell. Contemplated bacterial host cells include at least the genus of *Agrobacterium, Rhizobium, Bacillus, Brevibacillus, Escherichia, Pseudomonas, Klebsiella, Pantoea, Paenarthrobacter*, and *Erwinia*. In certain embodiments, the *Bacillus* species is a *Bacillus cereus* or *Bacillus thuringiensis*, the *Brevibacillus* is a *Brevibacillus laterosporus*, or the *Escherichia* is an *Escherichia coli*. Contemplated plant host cells include a dicotyledonous plant cell and a monocotyledonous plant cell. Contemplated plant cells further include an alfalfa, banana, barley, bean, broccoli, cabbage, brassica (e.g. canola), carrot, cassava, castor, cauliflower, celery, chickpea, Chinese cabbage, citrus, coconut, coffee, corn, clover, cotton (*Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In another embodiment, the pesticidal protein exhibits activity against Hemipteran insects, including, at least, Southern Green Stink Bug (*Nezara viridula*), Neotropical Brown Stink Bug (*Euschistus heros*), and Western tarnished plant bug (*Lygus hesperus*).

In another embodiment, the pesticidal protein exhibits activity against Lepidopteran insects, including, at least, Southern armyworm (*Spodoptera eridania*) and Soybean looper (*Chrysodeixis includens*).

Also contemplated in this application are bacteria and plants and plant parts comprising a recombinant nucleic acid molecule encoding the pesticidal proteins TIC11207 and TIC11304 or fragments thereof. The recombinant molecule (e.g. construct) may comprise a heterologous promoter for expression in bacterial or plant cells of the operably linked polynucleotide segment encoding the pesticidal protein. Both dicotyledonous plants and monocotyledonous plants are contemplated. In another embodiment, the plant is further selected from the group consisting of an alfalfa, banana, barley, bean, broccoli, cabbage, brassica (e.g. canola), carrot, cassava, castor, cauliflower, celery, chickpea, Chinese cabbage, citrus, coconut, coffee, corn, clover, cotton (i.e. *Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, corn (i.e. maize) such as sweet corn or field corn, sweet gum, sweet potato, switchgrass, tea, tobacco, tomato, triticale, turf grass, watermelon, and wheat. The plant parts may for instance include, without limitation, leaves, tubers, roots, stems, seeds, embryos, flowers, inflorescences, bolls, pollen, fruit, animal feed, and biomass. Processed plant parts, for instance wood, or oil, non-viable ground seeds or fractionated seeds, flour, or starch produced from the plant leaves, flowers, roots, seeds or tubers containing the nucleic acids encoding the proteins of the present invention, and/or containing pesticidally effective amounts of the encoded toxin proteins, are also contemplated.

In certain embodiments, seeds comprising the recombinant nucleic acid molecules and pesticidally effective amounts of the TIC11207 and TIC11304 toxin proteins, are disclosed.

In still another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. In certain embodiments, the at least one other pesticidal agent is selected from the group consisting of an insect inhibitory protein, an insect inhibitory dsRNA molecule, and an ancillary protein. It is also contemplated that the at least one other pesticidal agent in the insect inhibitory composition exhibits activity against one or more pest species of the orders Lepidoptera, Coleoptera, or Hemiptera. The at least one other pesticidal agent in the insect inhibitory composition is, in one embodiment, selected from the group consisting of a Cry1A, Cry1Ab, Cry1Ac, Cry1A.105, Cry1Ac, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ac, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, TIC4029, TIC4064, TIC13085, TIC13087, VIP3A, VIP3B, VIP3Ab, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-RI and variants thereof, IP3 and variants thereof, DIG-3, DIG-5, DIG-10, DIG-657, DIG-11 protein, IPD102Aa and homologs thereof, IPD110Aa and homologs thereof, TIC868, Cry1Da1_7, BCW003, TIC1100, TIC867, TIC867_23, TIC6757. TIC7641, TIC5290, TIC3668, TIC3669, TIC3670, IPD072Aa and homologs thereof, IPD103 and homologs thereof, PIP-50 and PIP-65 and homologs thereof, PIP-83 and homologs thereof, and Cry1B.34; and dsRNA mediated gene suppression embodiments including those targeting for suppression *Diabrotica* species genes Dv snf7 and Dv ssj1.

Commodity products comprising a detectable amount of the recombinant nucleic acid molecules and toxin proteins disclosed in this application are also contemplated. Such commodity products include commodity corn bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of this application, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

Also contemplated in this application is a method of producing seed comprising recombinant nucleic acid molecules and pesticidally effective amounts of the encoded TIC11207 and TIC11304 toxin proteins. The method comprises planting at least one seed comprising the recombinant nucleic acid molecules disclosed in this application; growing a plant from the seed; and harvesting seed from the plant, wherein the harvested seed comprises the referenced recombinant nucleic acid molecules and/or pesticidally effective amounts of the encoded TIC11207 and TIC11304 toxin proteins.

In another illustrative embodiment, a plant resistant to Hemipteran or Lepidopteran insect infestation, is provided wherein the cells of said plant comprise the recombinant nucleic acid molecules disclosed herein.

Also disclosed in this application are methods for controlling a Hemipteran or Lepidopteran species pest and controlling a Hemipteran or Lepidopteran species pest infestation of a plant, particularly a crop plant. The method comprises, in one embodiment, first contacting the pest with an insecticidally effective amount of a pesticidal protein as set forth in SEQ ID NOs: 2, 4, 12, or 14; or contacting the pest with an insecticidally effective amount of one or more pesticidal proteins comprising an amino acid sequence having at least 80%, or 85%, or 90%, or 95%, or about 100% amino acid sequence identity to SEQ ID NOs: 2, 4, 12, or 14.

Further provided herein is a method of detecting the presence of a recombinant nucleic acid molecule of the TIC11207 and TIC11304 toxin proteins class wherein the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein, and does not hybridize under such hybridization conditions with genomic DNA from an otherwise isogenic plant that does not comprise the segment, wherein the probe is homologous or complementary to SEQ ID NOs: 3, 5, 6, 7, 8, 9, 10, 13, or 15, or a sequence that encodes a pesticidal protein comprising an amino acid sequence having at least 80%, or 85%, or 90%, or 95%, or about 100% amino acid sequence identity to SEQ ID NOs: 2, 4, 12, or 14; subjecting the sample and probe to stringent hybridization conditions; and detecting hybridization of the probe with DNA of the sample.

Also provided herein are methods of detecting the presence of the pesticidal protein or fragment thereof from the TIC11207 and TIC11304 toxin proteins class wherein the method comprises contacting a sample with a TIC11207 and TIC11304 toxin proteins class immunoreactive antibody or recombinant protein designed for detecting the TIC11207 and TIC11304 proteins, and detecting the binding of the antibody to the TIC11207 and TIC11304 toxin protein class proteins, thus confirming the presence of the protein in the sample. In some embodiments the step of detecting comprises an ELISA, or a Western blot.

Also contemplated in this application is a method for controlling a Hemipteran or Lepidopteran pest species or pest infestation in a field wherein the method comprises growing a crop plant which expresses an insecticidally effective amount of a pesticidal protein as set forth in SEQ ID NOs: 2, 4, 12, 14, 17, or 19; or growing a crop plant which expresses an insecticidally effective amount of one or more pesticidal proteins comprising an amino acid sequence having at least 80%, or 85%, or 90%, or 95%, or about 100% amino acid sequence identity to SEQ ID NOs: 2, 4, 12, 14, 17, or 19; and releasing into the field with crops containing a gene encoding the toxin protein of the present invention, one or more transgenic Hemipteran or Lepidopteran pest species each carrying a self-limiting gene, for the purpose of preventing or delaying the onset of resistance of the one or more Hemipteran or Lepidopteran pest species to the toxin protein. In one embodiment, the crop plants can be monocotyledonous or dicotyledonous. In another embodiment, the dicotyledonous crop plant can be soybean, cotton, or canola the monocotyledonous crop plants can be corn, wheat, sorghum, rice, rye, or millet. In yet another embodiment, the monocotyledonous crop plants can be corn, wheat, sorghum, rice, rye, or millet.

BRIEF DESCRIPTION OF THE SEQUENCES

SEQ ID NO: 1 is a nucleic acid sequence encoding a TIC11207 pesticidal protein obtained from *Paenarthrobacter nitroguajacolicus* strain MDI-0030264.

SEQ ID NO:2 is the amino acid sequence of the TIC11207 pesticidal protein encoded by the sequence set forth in SEQ ID NO:1.

SEQ ID NO:3 is a synthetic coding sequence, TIC11207PL-1 encoding a TIC11207PL pesticidal protein and capable of use in a plant cell, wherein an additional codon encoding an alanine residue is inserted immediately following the initiating methionine codon.

SEQ ID NO:4 is the amino acid sequence of the TIC11207PL pesticidal protein encoded by SEQ ID NOs: 3, 5, 6, 7, 8, 9, and 10, wherein an additional alanine residue is inserted immediately following the initiating methionine.

SEQ ID NO:5 is a synthetic coding sequence, TIC11207PL-2 encoding a TIC11207PL pesticidal protein and capable of use in a plant cell, wherein an additional codon encoding an alanine residue is inserted immediately following the initiating methionine codon.

SEQ ID NO:6 is a synthetic coding sequence, TIC11207PL-3 encoding a TIC11207PL pesticidal protein and capable of use in a plant cell, wherein an additional codon encoding an alanine residue is inserted immediately following the initiating methionine codon.

SEQ ID NO:7 is a synthetic coding sequence, TIC11207PL-4 encoding a TIC11207PL pesticidal protein and capable of use in a plant cell, wherein an additional codon encoding an alanine residue is inserted immediately following the initiating methionine codon.

SEQ ID NO:8 is a synthetic coding sequence, TIC11207PL-5 encoding a TIC11207PL pesticidal protein and capable of use in a plant cell, wherein an additional codon encoding an alanine residue is inserted immediately following the initiating methionine codon.

SEQ ID NO:9 is a synthetic coding sequence, TIC11207PL-6 encoding a TIC11207PL pesticidal protein and capable of use in a plant cell, wherein an additional codon encoding an alanine residue is inserted immediately following the initiating methionine codon.

SEQ ID NO:10 is a synthetic coding sequence, TIC11207PL-7 encoding a TIC11207PL pesticidal protein and capable of use in a plant cell, wherein an additional codon encoding an alanine residue is inserted immediately following the initiating methionine codon.

SEQ ID NO:11 is a nucleic acid sequence encoding a TIC11304 pesticidal protein obtained from *Paenarthrobacter nitroguajacolicus* strain MDI-0030376.

SEQ ID NO: 12 is the amino acid sequence of the TIC11304 pesticidal protein encoded by the sequence set forth in SEQ ID NO: 11.

SEQ ID NO: 13 is a synthetic coding sequence, TIC11304PL-1 encoding a TIC1304PL pesticidal protein and capable of use in a plant cell, wherein an additional codon encoding an alanine residue is inserted immediately following the initiating methionine codon.

SEQ ID NO:14 is the amino acid sequence of the TIC11304PL pesticidal protein encoded by SEQ ID NOs: 13 and 15, wherein an additional alanine residue is inserted immediately following the initiating methionine.

SEQ ID NO: 15 is a synthetic coding sequence, TIC11304PL-2 encoding a TIC11304PL pesticidal protein and capable of use in a plant cell, wherein an additional codon encoding an alanine residue is inserted immediately following the initiating methionine codon.

SEQ ID NO:16 is a nucleic acid sequence encoding TIC11207 pesticidal protein with a Histidine tag operably linked to the 3' end, herein referred to asTIC11207-His.

SEQ ID NO:17 is the amino acid sequence of the TIC11207-His protein encoded by SEQ ID NO: 16.

SEQ ID NO:18 is a nucleic acid sequence encoding TIC11304 pesticidal protein with a Histidine tag operably linked to the 3' end, herein referred to asTIC11304-His.

SEQ ID NO: 19 is the amino acid sequence of the TIC11304-His protein encoded by SEQ ID NO: 18.

BRIEF DESCRIPTION OF THE FIGURES

FIG. 1 depicts an alignment of the pesticidal toxins TIC11207 (SEQ ID NO: 2), TIC11304 (SEQ ID NO: 12), and APG01463 (SEQ ID NO: 20) presented in United States patent application publication US20180066277. Identical amino acids are identified by an asterisk in the multi-alignment.

DETAILED DESCRIPTION OF THE INVENTION

Figure 2:
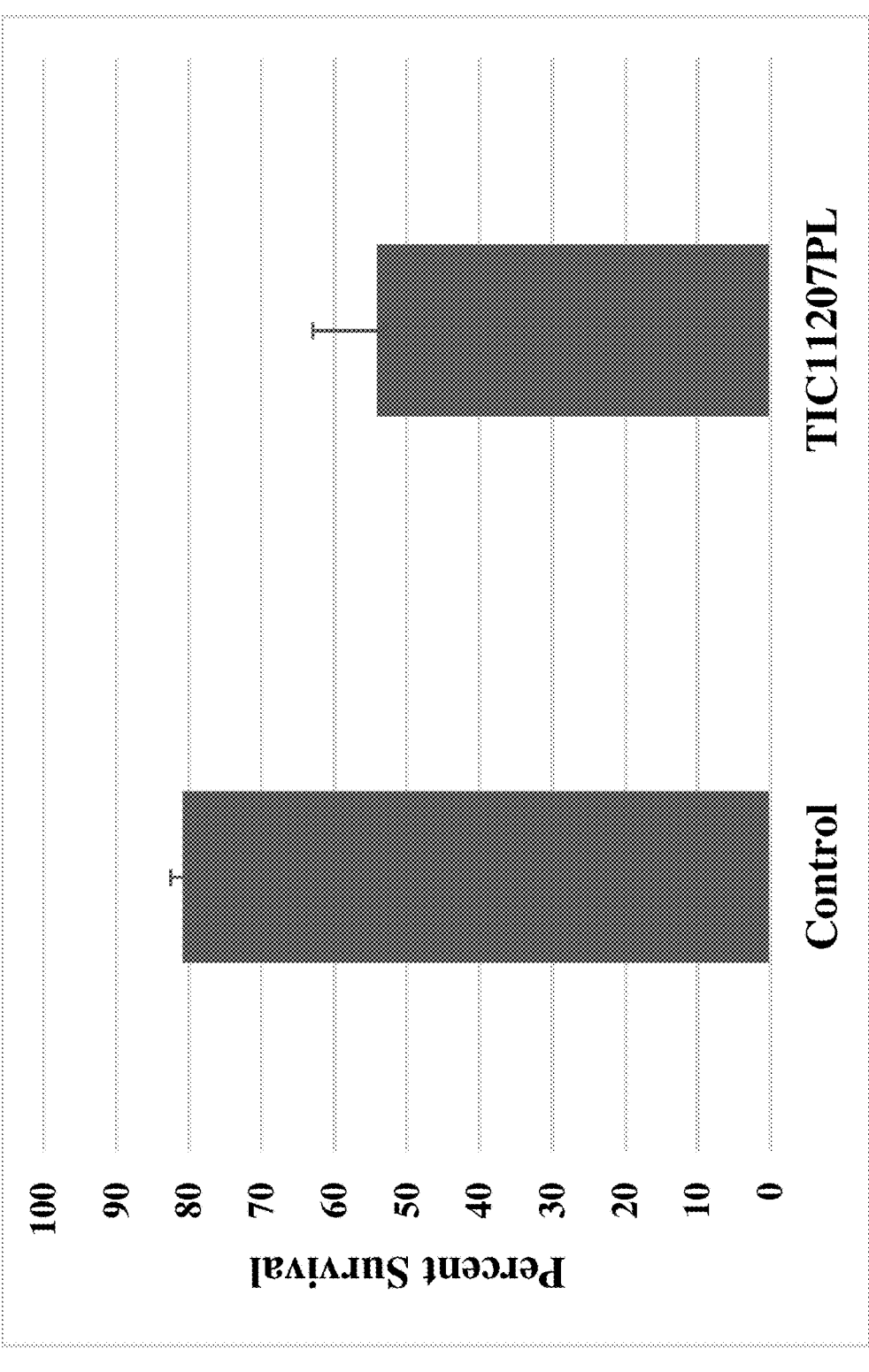
FIG. 2 is a graphical representation of the mean percent survivorship of Neotropical Brown Stink Bug (*Euschistus heros*) when feeding on stably transformed soybean plants expressing the TIC11207PL protein. The control plants are wild-type untransformed soybean plants.

One problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Two novel pesticidal proteins exemplified by TIC11207 and TIC11304 are disclosed herein. Use of the proteins in pesticidally effective amounts can address insect infestations that are problems in the art, particularly against a spectrum of Hemipteran insect pests, and more particularly against Southern Green Stink Bug (*Nezara viridula*), Neotropical Brown Stink Bug (*Euschistus heros*), and Western tarnished plant bug (*Lygus hesperus*), as well as, Lepidopteran insect pests, more particularly, Southern armyworm (*Spodoptera eridania*) and Soybean looper (*Chrysodeixis includens*).

Reference in this application to TIC11207, "TIC11207 protein", "TIC11207 protein toxin", "TIC11207 pesticidal protein", "TIC11207-related toxins", "TIC11207-related toxins". "TIC11207 protein toxin class", "TIC11207 toxin protein class" and the like, refer to any novel pesticidal protein or insect inhibitory protein, that comprises, that consists of, that is substantially homologous to, that is similar to, or that is derived from any pesticidal protein or insect inhibitory protein sequence of TIC11207 (SEQ ID NO:2). Reference in this application to TIC11304, "TIC11304 protein", "TIC11304 protein toxin", "TIC11304 pesticidal protein", "TIC11304-related toxins", "TIC11304-related toxins". "TIC11304 protein toxin class", "TIC11304 toxin protein class" and the like, refer to any novel pesticidal protein or insect inhibitory protein, that comprises, that consists of, that is substantially homologous to, that is similar to, or that is derived from any pesticidal protein or insect inhibitory protein sequence of TIC11304 (SEQ ID NO:12).

The term "segment" or "fragment" is used in this application to describe consecutive amino acid or nucleic acid sequences that are shorter than the complete amino acid or nucleic acid sequence describing the TIC11207, TIC11207PL, TIC11304, and TIC11304PL proteins. A segment or fragment exhibiting insect inhibitory activity is also disclosed in this application if alignment of such segment or fragment, with the corresponding section of the TIC11207, TIC11207PL, TIC11304, and TIC11304PL proteins set forth in SEQ ID NOs: 2, 4, 12, and 14, respectively, results in amino acid sequence identity of any fraction percentage from about 80% to about 100% between the segment or fragment and the corresponding segment of amino acids within the TIC11207, TIC11207PL, TIC11304, and TIC11304PL proteins.

Reference in this application to the terms "active" or "activity", "pesticidal activity" or "pesticidal" or "insecticidal activity", "insect inhibitory", "pesticidally effective" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop) containing an effective amount of the TIC11207, TIC11207PL, TIC11304, or TIC11304PL protein or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopterans, as well as protein toxins that are used to control other plant pests such as Cry, Vip, and Cyt proteins, *Pseudomonas* insect toxic proteins, and insect toxin proteins derived from fern species, that are available in the art for use in controlling Lepidopteran, Coleopteran, Dipteran, Hemipteran and Homopteran species.

It is intended that reference to a pest, particularly a pest of a crop plant, means insect pests of crop plants, particularly those Hemiptera and Lepidoptera insect pests that are controlled by the TIC11207 and TIC11304 protein toxins class. However, reference to a pest can also include Coleopteran, Hemipteran, Lepidopteran, Dipteran, and Homopteran insect pests of plants, as well as nematodes and fungi when toxic agents targeting these pests are co-localized or present together with the TIC11207 and TIC11304 proteins or a protein that is 80 to about 100 percent identical to TIC11207 and TIC11304 proteins. The phrases "present together" or "co-localized" are intended to include any instance of which a target insect pest has been contacted by a TIC11207 and TIC11304 toxin proteins as well as any other toxic agent also present in a pesticidally effective amount relative to the target insect pest. "Contacted" is intended in certain embodiments to refer to being present in the diet of the target pest, and the diet is consumed by the target pest.

The insects of the order Hemiptera include, but are not limited to, Stink Bugs of the family Pentatomidae: Green Stink Bugs from the genus *Chinavia* (*Chinavia hilaris, Chinavia marginata*, and *Chinavia pensylvanica*), Stink bugs of the genus *Chlorochroa* (*Chlorochroa* granulose, *Chlorochroa kanei, Chlorochroa ligata, Chlorochroa lineate, Chlorochroa opuntiae, Chlorochroa persimilis, Chlorochroa rossiana, Chlorochroa sayi, Chlorochroa uhleri, Chlorochroa belfragii, Chlorochroa faceta, Chlorochroa osborni, Chlorochroa saucia*, and *Chlorochroa senilis*), Southern Green Stink Bug (*Nezara viridula*), Stink Bugs from the genus *Edessa* (*Edessa meditabunda, Edessa bifida*, and *Edessa florida*), the Neotropical Brown Stink Bug (*Euschistus heros*), stink bugs from the genus *Euschistus* (*Euschistus acuminatus, Euschistus biformis, Euschistus conspersus, Euschistus crenator, Euschistus egglestoni, Euschistus ictericus, Euschistus inflatus, Euschistus latimarginatus, Euschistus obscures, Euschistus politus, Euschistus quadrator, Euschistus sevus, Euschistus strenuous, Euschistus tristigmus*, and *Euschistus variolarius*), Brown Marmorated Stink Bug (*Halyomorpha halys*), Red-Shouldered Stink Bug (*Thyanta accerra*), stink bugs of the genus *Thyanta* (*Thyanta calceata, Thyanta custator, Thyanta pallidovirens, Thyanta perditor, Thyanta maculate*, and *Thyanta pseudocasta*), the Green Belly Stink Bug (*Dichelops melacanthus*) and other stink bugs of the genus *Dichelops* (*Dichelops avilapiresi, Dichelops bicolor, Dichelops dimidatus, Dichelops furcatus, Dichelops furcifrons, Dichelops lobatus, Dichelops miriamae, Dichelops nigrum, Dichelops peruanus, Dichelops phoenix*, and *Dichelops saltensis*), the Red Banded Stink Bug (*Piezodorus guildinni*) as well as *Piezodorus lituratus*; insects of the family of Plataspidae such as, but not limited to, Kudzu Bug (*Megacopta cribraria*), Western tarnished plant bug (*Lygus hesperus*), Tarnished plant bug (*Lygus lineolaris*); aphid species such as, but not limited to, Soybean aphid (*Aphis glycines*), Green Peach aphid (*Myzus persicae*), Potato aphid (*Macrosiphum euphorbiae*), Melon aphid (*Aphis gossypii*), Cabbage aphid (*Brevicoryne brassicae*); whitefly pest species, such as but not limited to, Greenhouse whitefly (*Trialeurodes vaporariorum*), Sweet potato whitefly (*Bemisia tabaci*), Giant whitefly (*Aleurodicus dugesii*); and Planthopper species such as, but not limited to, Blue-green leafhopper (*Graphocephala atropunctata*) and Ligurian leafhopper (*Eupteryx decemnotata*).

The insects of the order Lepidoptera include, but are not limited to, armyworms, cutworms, loopers, and heliothines in the Family Noctuidae, e.g., Fall armyworm (*Spodoptera frugiperda*), Beet armyworm (*Spodoptera exigua*), Black armyworm (*Spodoptera cosmioides*), Southern armyworm (*Spodoptera eridania*), bertha armyworm (*Mamestra configurata*), black cutworm (*Agrotis ipsilon*), cabbage looper worm (*Trichoplusia ni*), Sugarcane borer (, *Diatraea* saccharalis), soybean looper (*Pseudoplusia includens*), Sunflower looper (*Rachiplusia nu*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), Sunflower looper (*Rachiplusia nu*), South American podworm (*Helicoverpa gelotopoeon*) western cutworm (*Agrotis orthogonia*); borers, casebearers, webworms, coneworms, cabbageworms and skeletonizers from the Family Pyralidae, e.g., European corn borer (*Ostrinia nubilalis*), navel orange worm (*Amyelois transitella*), corn root webworm (*Crambus caliginosellus*), sod webworm (*Herpetogramma licarsisalis*), sunflower moth (Homoeosoma electellum), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*), and gypsy moth (*Lymantria dispar*). Other insect pests of order Lepidoptera include, e.g., cotton leaf worm (*Alabama argillacea*), fruit tree leaf roller (*Archips argyrospila*), European leafroller (*Archips* rosana) and other *Archips* species, (*Chilo suppressalis*, Asiatic rice borer, or rice stem borer), rice leaf roller (*Cnaphalocrocis medinalis*), corn root webworm (*Crambus caliginosellus*), bluegrass webworm (*Crambus teterrellus*), southwestern corn borer (*Diatraea grandiosella*), sugarcane borer (*Diatraea* saccharalis), spiny bollworm (*Earias insulana*), spotted bollworm (*Earias vittella*), American bollworm (*Helicoverpa armigera*), corn earworm (*Helicoverpa zea*, also known as soybean podworm and cotton bollworm), tobacco budworm (*Heliothis virescens*), sod webworm (*Herpetogramma licarsisalis*), Western bean cutworm (*Striacosta albicosta*), European grape vine moth (*Lobesia botrana*), citrus leafminer (*Phyllocnistis citrella*), large white butterfly (*Pieris brassicae*), small white butterfly (*Pieris rapae*, also known as imported cabbageworm), beet armyworm (*Spodoptera exigua*), tobacco cutworm (*Spodoptera litura*, also known as cluster caterpillar), and tomato leaf miner (*Tuta absoluta*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any trans-genic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

Reference in this application to the term "self-limiting gene" refers to a gene that limits survival of the host, resulting in a reduction in the host population. Such technology is offered by Oxitech Ltd. Transgenic male insects carrying a transgenic self-limiting gene are released and reproduce with wild females. As a result, the progeny inherit a copy of the self-limiting gene. The self-limiting gene disrupts the proper functioning of the insects' cells by over-producing a protein in them, interfering with the cells' ability to produce other essential proteins needed for development. By disrupting the insect's normal development, the gene prevents it from surviving to adulthood. For example, the self-limiting Diamondback Moth (*Plutellidae xylostella*) strain OX4319L was developed by Oxitech Ltd and carries a male-selecting gene that utilizes sequences from the sex determination gene doublesex (dsx). The gene expresses sex-alternate splicing, to engineer female-specific expression of the self-limiting gene which prevents survival of female offspring beyond the larval stage and allows for production of male only cohorts of self-limiting moths. After being released, males mate with pest females, leading to a reduction in the number of female offspring in the next generation, thereby locally suppressing *P. xylostella* populations. To facilitate the rearing of large numbers of males for release within diamondback moth production facilities, the expression of female-specific dsx within the OX4319L strain is repressed by the addition of tetracycline, or suitable analogs, into the larval feed. OX4319L also expresses the fluorescent protein, DsRed, to permit the effective monitoring of the presence of this strain in the field (Jin et al., 2013. Engineered female-specific lethality for control of pest Lepidoptera. ACS Synthetic Biology, 2:160-166). This technology, when applied in the field with plants containing the toxin genes of the present invention, can delay or prevent the onset of resistance of pest species targeted for control by the toxin genes and proteins of the present invention, thus giving a greater durability of any plant product containing the toxin genes and proteins of the present invention.

While self-limiting technologies have not yet been developed to control Hemipteran insect pests, some of the key genes in sex determination have been identified and the differential splicing of their transcripts between the sexes determined for the Hemipteran species brown planthopper (*N. lugens*), the whitefly (*B. tabaci*), and the kissing bug (*Rhodnius prolixus*). More research is needed before sex ratios can be altered as part of a genetic-control strategy. Some hemipteran species, such as whiteflies, are haplodiploid and others lack Y chromosomes. These alternative genetic systems will, most likely, influence the design and efficiencies of genetic-control mechanisms such as self-limiting technologies. While many of the attributes that make Diptera and Lepidoptera amenable to genetic-control mechanisms, many of these constraints are not insurmountable. Current control strategies will need to be adapted or new strategies developed to enable the field of hemipteran control. Within the past 4 years, there have been substantial advances in the field of hemipteran biotechnology. The enabling technology of CRISPR/Cas-meditated mutagenesis in the Hemiptera is emerging. The increasing numbers of annotated genome assemblies now provide essential components for the development of the genetic toolbox required for extended genetic control into Hemipteran pests (Pacheco et al., (2022) Gene Editing and Genetic Control of Hemipteran Pests: Progress, Challenges and Perspectives, Frontiers in Bioengineering and Biotechnology, 10:1-26).

As described further in this application, an open reading frame (ORF) encoding TIC11207 (SEQ ID NO:1) was discovered in DNA obtained from *Paenarthrobacter nitroguajacolicus* strain MDI-0030264. Bioassay using microbial host cell-derived proteins of TIC11207 demonstrated activity against the Hemipteran species Green Stink Bug (*Nezara viridula*), Neotropical Brown Stink Bug (*Euschistus heros*), and Western tarnished plant bug (*Lygus hesperus*). Also describe further in this application is an open reading frame (ORF) encoding TIC11304 (SEQ ID NO:11) that was discovered in DNA obtained from *Paenarthrobacter nitroguajacolicus* strain MDI-0030376. Bioassay using microbial host cell-derived proteins of TIC11304 demonstrated activity against the Hemipteran species Green Stink Bug (*Nezara viridula*), Neotropical Brown Stink Bug (*Euschistus heros*), and Western tarnished plant bug (*Lygus hesperus*), as well as the Lepidopteran pest species Southern armyworm (*Spodoptera eridania*) and Soybean looper (*Chrysodeixis includens*).

Synthetic coding sequences designed for use in a plant cell were produced to express TIC11207PL, the TIC11207 amino acid sequence wherein an additional alanine residue is inserted immediately following the initiating methionine, encoded by SEQ ID NOs: 3, 5, 6, 7, 8, 9, and 10. Synthetic coding sequences were also designed for use in a plant cell to express TIC11304PL, the TIC11304 amino acid sequence wherein an additional alanine residue is inserted immediately following the initiating methionine, encoded by SEQ ID NOs: 13 and 15. These coding sequences were operationally/functionally linked to a plant functional promoter and other elements that function in plants to mediate the desired level and spatial properties for expression in plants. Soybean plants expressing TIC11207PL demonstrated efficacious activity against the Hemipteran species Neotropical Brown Stink Bug (*Euschistus heros*).

For expression in plant cells, the TIC11207, TIC11207PL, TIC11304, and TIC11304PL (SEQ ID NOs: 2, 4, 12, 14) proteins can be expressed and localized in the cytosol or targeted to various organelles of the plant cell. For example, targeting a protein to the chloroplast may result in increased levels of expressed protein in a transgenic plant while preventing off-phenotypes from occurring if the expressed protein toxin reacts with the cell biology in any unexpected manner. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids in length. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated CTPs include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the TIC11207, TIC11207PL, TIC11304, or TIC11304PL toxin proteins to the chloroplast, a sequence encoding a chloroplast transit peptide is placed 5' in operable linkage and in frame to a sequence that has been designed for expression in plant cells to encode any of the toxin proteins TIC11207, TIC11207PL, TIC11304, or TIC11304PL.

It is contemplated that improved variants of the TIC11207 and TIC11304 protein toxins class can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence may be altered to engineer a new protein amino acid sequence. Alternatively, a fragment within the coding sequence may be replaced or deleted, or additional DNA fragments are inserted into the coding sequence, to engineer a new toxin coding sequence. The new coding sequence can encode a toxin protein with new properties such as increased activity or spectrum against insect pests, as well as provide activity against one or more insect pest species wherein resistance has developed or likely to arise against the original insect toxin protein. The plant cell comprising the gene edited toxin coding sequence can be used by methods known in the art to generate whole plants expressing the new toxin protein.

For each of TIC11207, TIC11207PL, TIC11304, and TIC11304PL, fragments and amino acid sequence variants that retain or that exhibit improved insect inhibitory activity are contemplated. Variants thereof can be truncated forms wherein one or more amino acids are deleted from the N-terminal end, C-terminal end, the middle of the protein, or combinations thereof wherein the variants retain or exhibit improved insect inhibitory activity compared to the naturally occurring sequence. These fragments can be naturally occurring or synthetic (artificial) variants of TIC11207, TIC11207PL, TIC11304, or TIC11304PL or derived protein variants but should retain at least the insect inhibitory activity of TIC11207, TIC11207PL, TIC11304, or TIC11304PL.

Proteins that resemble the TIC11207 and TIC11304 proteins can be identified and compared to each other using various computer-based algorithms known in the art. Amino acid sequence identities reported in this application are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment and are contemplated herein.

It is intended that a protein exhibiting insect inhibitory activity against a Hemipteran or Lepidopteran insect species is related to TIC11207 and TIC11304 if the protein is used in a query, e.g., in a Clustal W alignment, and the proteins of the present invention as set forth in SEQ ID NOs: 2 or 12 are identified as hits in such an alignment in which the query protein exhibits at least 80% to about 100% amino acid identity along the length of the query protein is about 80%, 81%, 82%, 83%, 84%, 85%, 86%, 87%, 88%, 90%, 91%, 92%, 93%, 94%, 95%, 96%, 97%, 98%, 99%, 100%, or any fraction in this range.

The closest identity match to the amino acid sequences of TIC11207 and TIC11304 has been disclosed in United States patent application publication US20180066277 as insect toxin protein, APG01463 (SEQ ID NO:42) which is 80% and 78.1% identical to TIC11207 and TIC11304, respectively. FIG. 1 shows a multi-alignment from a Clustal W analysis of TIC11207, TIC11304, and APG01463. APG01463 demonstrated activity against Fall armyworm (*Spodoptera frugiperda*) but did not demonstrate activity against Southern Green Stink Bug (*Nezara viridula*) or Soybean aphid (*Aphis glycines*). Table 1 below shows a multi-alignment using Clustal W for TIC11207, TIC11304, and APG01463 wherein the numbers in parathesis are the numbers of identical amino acids.

TABLE 1

| Percent identity of TIC11207, TIC11304, and APG01463. | | | |
|---|---|---|---|
| Toxin | TIC11207 | TIC11304 | APG01463 |
| TIC11207 | — | 96.6 (313) | 79 (256) |
| TIC11304 | 96.6 (313) | — | 77.2 (250) |
| APG01463 | 80 (256) | 78.1 (250) | — |

In addition to percent identity, TIC11207 and TIC11304 can also be related by primary structure (conserved amino acid motifs), by length and by other characteristics. Characteristics of the TIC11207 and TIC11304 pesticidal proteins are reported in Table 2 below.

redundancy of the genetic code, it is within the skill of the art to produce any number of other sequences for encoding the toxin proteins however, it is understood that the sequences produced for expression in planta should avoid known problems in the art that hinder or limit the efficient expression of the coding sequence, particularly as described in U.S. Pat. No. 5,500,365.

Expression cassettes and vectors containing a recombinant nucleic acid sequence molecule can be constructed and introduced into plants, particularly such as corn, soybean, or cotton plant cells in accordance with transformation methods and techniques known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257A1 (sugar beet), U.S. Pat. No. 5,750,871 (canola), 7,026,528 (wheat), and 6,365,807 (rice), and in Arencibia et al. (1998) Transgenic Res. 7:213-222 (sugarcane) all of which are incorporated herein by reference in their entirety. Transformed cells can be regenerated into transformed plants that express TIC2199 and demonstrate pesticidal activity through bioassays performed in the presence of Lepidopteran pest larvae using plant leaf disks obtained from the transformed plants. Plants can be derived from the plant cells by regeneration, seed, pollen, or meristem transformation techniques. Methods for transforming plants are known in the art.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand

TABLE 2

| | Selected characteristics of the TIC11207 and TIC11304 pesticidal proteins. | | | | | | | |
|---|---|---|---|---|---|---|---|---|
| Protein | Molecular Weight (in Daltons) | Amino Acid Length | Isoelectric Point | Charge at PH 7.0 | No. of Hydrophobic Amino Acids | No. of Polar Amino Acids | No. of Strongly Basic (—) Amino Acids | No. of Strongly Acidic Amino Acids |
| TIC11207 | 34538.39 | 324 | 4.7597 | −8.5 | 175 | 149 | 30 | 35 |
| TIC11304 | 34459.33 | 324 | 4.6638 | −9.0 | 178 | 146 | 28 | 34 |

As described further in the Examples of this application, synthetic nucleic acid coding sequences encoding TIC11207 and TIC11304 were designed for use in plants, encoded by SEQ ID NOs: 3, 5, 6, 7, 8, 9, 10, 13, and 15. In view of the break (DSB) or nick at a desired genomic site or locus. Briefly as understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cas12a). For methods using RNA-guided site-specific nucleases (e.g., Cas9 or Cas12a), the recombinant DNA construct(s) will also comprise a sequence encoding one or more guide RNAs to direct the nuclease to the desired site within the plant genome.

Recombinant nucleic acid molecule compositions that encode bacterial and plant expressed TIC11207 and TIC11304 proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to a TIC11207 or TIC11304 protein encoding sequence for expression of the protein in plants or a Bt-functional promoter operably linked to a TIC11207 or TIC11304 protein encoding sequence for expression in of the protein in Bt bacterium or other *Bacillus* species. Other element can be operably linked to the TIC11207 and TIC11304 protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NOs: 1, 3, 5, 6, 7, 8, 9, 10, 11, 13, 15, 16, and 18 that encodes a TIC11207 or TIC11304 protein having the amino acid sequences as set forth in SEQ ID NOs: 2, 4, 12, 14, 17, and 19. SEQ ID NOs: 16 and 18 encode TIC11207_His (SEQ ID NO:17) and TIC11304-His (SEQ ID NO:19), respectively which comprises a Histidine tag at the carboxy terminus allowing for expression in *E. coli* for isolation and purification. A heterologous promoter can also be operably linked to a synthetic coding sequence encoding a plastid targeted TIC11207 or TIC11304. The codons of a recombinant nucleic acid molecule encoding proteins disclosed herein can be substituted by synonymous codons (known in the art as a silent substitution).

A recombinant DNA construct comprising TIC11207 or TIC11304 protein encoding sequences can further comprise a region of DNA that encodes for one or more insect inhibitory agents which can be configured to concomitantly express or co-express with a DNA sequence encoding a TIC11207 or TIC11304 protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent. A recombinant DNA construct can be assembled so that all proteins or dsRNA molecules are expressed from one promoter or each protein or dsRNA molecule is under separate promoter control or some combination thereof. The proteins of this invention can be expressed from a multi-gene expression system in which TIC11207 or TIC11304 is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked or linked expression cassettes, each cassette expressing a different protein or other agent such as one or more dsRNA molecules.

Recombinant polynucleotides or recombinant DNA constructs comprising a TIC2199 protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC11207 or TIC11304 protein encoding sequence in a host cell, or subsequent expression of the encoded polypeptide. An exogenous recombinant polynucleotide or recombinant DNA construct that comprises a TIC11207 or TIC11304 protein encoding sequence and that is introduced into a host cell is referred in this application as a "transgene".

Transgenic bacteria, transgenic plant cells, transgenic plants, and transgenic plant parts that contain a recombinant polynucleotide that expresses TIC11207 or TIC11304 or a related family toxin protein encoding sequence are provided herein. The term "bacterial cell" or "bacterium" can include, but is not limited to, an *Agrobacterium*, a *Bacillus*, an *Escherichia*, a *Salmonella*, a *Pseudomonas, Brevibacillus, Klebsiella, Erwinia*, or a *Rhizobium* cell. The term "plant cell" or "plant" can include but is not limited to a dicotyledonous or monocotyledonous plant. The term "plant cell" or "plant" can also include but is not limited to an alfalfa, banana, barley, bean, broccoli, cabbage, brassica (e.g. canola), carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, corn (i.e. maize, such as sweet corn or field corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Lepidoptera-inhibitory or Hemipteran-inhibitory amounts of a TIC11207 or TIC11304 protein are provided. Such plants can be made by introducing a recombinant polynucleotide that encodes any of the proteins provided in this application into a plant cell, and selecting a plant derived from said plant cell that expresses an insect, Lepidoptera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of TIC11207 or TIC11304, an insect inhibitory segment or fragment thereof, or any distinguishing portion thereof, are also disclosed herein. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of TIC11207 or TIC11304.

Plants expressing the TIC11207 or TIC11304 protein can be crossed by breeding with transgenic events expressing other toxin proteins and/or expressing other transgenic traits such as herbicide tolerance genes, genes conferring yield or stress tolerance traits, and the like, or such traits can be combined in a single stacked vector so that the traits are all linked.

As further described in the Examples, TIC11207 or TIC11304 protein-encoding sequences and sequences having a substantial percentage identity to TIC11207 or TIC11304, can be identified using methods known to those of ordinary skill in the art such as polymerase chain reaction (PCR), thermal amplification, and hybridization. For example, the proteins TIC11207 and TIC11304 can be used to produce antibodies that bind specifically to related proteins and can be used to screen for and to find other protein members that are closely related.

Furthermore, nucleotide sequences encoding the TIC11207 or TIC11304 toxin protein can be used as probes and primers for screening to identify other members of the class using thermal-cycle or isothermal amplification and hybridization methods. For example, oligonucleotides derived from sequences as set forth in SEQ ID NOs: 3, 5, 6, 7, 8, 9, 10, 13, and 15 can be used to determine the presence or absence of a TIC11207 or TIC11304 transgene in a deoxyribonucleic acid sample derived from a commodity product. Given the sensitivity of certain nucleic acid detection methods that employ oligonucleotides, it is anticipated that oligonucleotides derived from sequences as set forth in SEQ ID NOs: 3, 5, 6, 7, 8, 9, 10, 13, and 15 can be used to detect a TIC11207 or TIC11304 transgene in commodity products derived from pooled sources where only a fraction of the commodity product is derived from a transgenic plant containing any of the transgenes. It is further recognized that such oligonucleotides can be used to introduce nucleotide sequence variation in each of SEQ ID NOs: 1, 3, 5, 6, 7, 8, 9, 10, 11, 13, 15, 16, and 18. Such "mutagenesis" oligonucleotides are useful for identification of TIC11207 and TIC11304 amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under stringent hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes to the second nucleotide sequence. In such case, the second nucleotide sequence can be any of the nucleotide sequences presented as of SEQ ID NOs: 1, 3, 5, 6, 7, 8, 9, 10, 11, 13, 15, 16, and 18 under stringent hybridization conditions. Nucleotide coding sequences hybridize to one another under appropriate hybridization conditions, such as stringent hybridization conditions, and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding such related proteins, and those sequences, to the extent that they function to express pesticidal proteins either in *Bacillus* strains or in plant cells, are embodiments of the present invention, recognizing of course that many such redundant coding sequences will not hybridize under these conditions to the native *Bacillus* sequences encoding TIC11207 and TIC11304 variants. This application contemplates the use of these, and other identification methods known to those of ordinary skill in the art, to identify TIC11207 and TIC11304 variant protein-encoding sequences and sequences having a substantial percentage identity to TIC11207 and TIC11304 variants protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC11207 and TIC11304 protein to derive additional useful embodiments including assembly of segments of TIC11207 and TIC11304 protein with segments of diverse proteins different from TIC11207 and TIC11304 protein and related proteins. The TIC11207 and TIC11304 proteins may be subjected to alignment to each other and to other *Paenarthrobacter, Bacillus, Paenibacillus* or other pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

Methods of controlling insects, in particular Hemipteran infestations of crop plants, with the TIC11207 or TIC11304 proteins are disclosed in this application. Such methods can comprise growing a plant comprising an insect- or Hemiptera-inhibitory amount of a TIC11207 or TIC11304 toxin protein. In certain embodiments, such methods can further comprise any one or more of: (i) applying any composition comprising or encoding a TIC11207 or TIC11304 toxin protein to a plant or a seed that gives rise to a plant; and (ii) transforming a plant or a plant cell that gives rise to a plant with a polynucleotide encoding a TIC11207 or TIC11304 toxin protein. In general, it is contemplated that a TIC11207 or TIC11304 toxin protein can be provided in a composition, provided in a microorganism, or provided in a transgenic plant to confer insect inhibitory activity against Hemipteran insects.

In certain embodiments, a recombinant nucleic acid molecule of TIC11207 or TIC11304 toxin protein is the insecticidally active ingredient of an insect inhibitory composition prepared by culturing recombinant *Bacillus* or any other recombinant bacterial cell transformed to express a TIC11207 or TIC11304 toxin protein under conditions suitable to express the TIC11207 or TIC11304 toxin protein. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising TIC11207 or TIC11304 protein can further comprise at least one additional polypeptide that exhibits insect inhibitory activity against the same Hemipteran or Lepidopteran insect species, but which is different from the TIC11207 or TIC11304 toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptides for the control of Hemipteran pests may be selected from the group consisting of an insect inhibitory protein, such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Further a polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI-220 (U.S. Patent Publication 2014-0245491A1), AXMI-2212, AXMI-223z (U.S. Patent Publication 2014-0196175 A1), AXMI-279 (U.S. Patent Publication 2014-0223599 A1), AXMI-RI and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092

A1), CHIPs (U.S. Patent Application Publication No. 2010/0017914 A1), IP3 and variants thereof (U.S. Patent Publication 2012-0210462 A1), IPD102Aa and homologs thereof (International Application Publication WO2020076958 A1), IPD110Aa and homologs thereof (U.S. Patent Application Publication No. 2021-0355174 A1), and □-Hexatoxin-Hvla (U.S. Patent Application Publication US2014-0366227 A1).

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Lepidopteran pests, combinations of insect inhibitory proteins of the present invention can be used with Lepidopteran-active proteins, such as, but not limited to, Cry1A (U.S. Pat. No. 5,880,275), Cry1Ab, Cry1Ac, Cry1A.105, Cry1Ac, Cry1B (U.S. Patent Publication Ser. No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392 (A2)), Cry2A, Cry2Ab (U.S. Pat. No. 7,064,249), Cry2Ac, Cry4B, Cry6, Cry7, Cry8, Cry9, Cry15, Cry43A, Cry43B, Cry51Aa1, ET66, TIC400, TIC800, TIC834, TIC1415, TIC2160, TIC3131, TIC836, TIC860, TIC867, TIC869, TIC1100, TIC4029, TIC4064, TIC13085, TIC13087, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-2212, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523 (A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), DIG-657 (International Application Publication WO2015/195594 A2), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NOs: 2 or 4 and derivatives thereof as described in U.S. Patent Publication 2012-0167259 A1, SEQ ID NOs: 2 or 4 and derivatives thereof as described in U.S. Patent Publication 2012-0047606 A1, SEQ ID NOs: 2 or 4 and derivatives thereof as described in U.S. Patent Publication 2011-0154536 A1, SEQ ID NOs: 2 or 4 and derivatives thereof as described in U.S. Patent Publication 2011-0112013 A1, SEQ ID NOs: 2 or 4 and 4 and derivatives thereof as described in U.S. Patent Publication 2010-0192256 A1, SEQ ID NOs: 2 or 4 and derivatives thereof as described in U.S. Patent Publication 2010-0077507 A1, SEQ ID NOs: 2 or 4 and derivatives thereof as described in U.S. Patent Publication 2010-0077508 A1, SEQ ID NOs: 2 or 4 and derivatives thereof as described in U.S. Patent Publication 2009-0313721 A1, SEQ ID NOs: 2 or 4 and derivatives thereof as described in U.S. Patent Publication 2010-0269221 A1, SEQ ID NOs: 2 or 4 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NOs: 2 or 4 and derivatives thereof as described in U.S. Pat. No. 7,510,878 (B2), SEQ ID NOs: 2 or 4 and derivatives thereof as described in U.S. Pat. No. 7,812,129 (B1), IPD072Aa and homologs thereof (U.S. Patent Application Publication No. 2016-0366891 A1) and IPD103 and homologs thereof (International Application Publication WO2018005411 A1), PIP-50 and PIP-65 and homologs thereof (U.S. Patent Application Publication No. 2017-0166921 A1), PIP-83 and homologs thereof (U.S. Patent Application Publication No. 2016-0347799 A1); and the like.

Additional polypeptides for the control of Coleopteran, Lepidopteran, and Hemipteran insect pests, which can be combined with the insect inhibitory proteins of the TIC11207 and TIC11304 class, can be found on the *Bacillus thuringiensis* toxin nomenclature website maintained by Neil Crickmore (on the world wide web at btnomenclature.info). Broadly, it is contemplated that any insect inhibitory protein known to those of ordinary skill in the art can be used in combination with the proteins of the TIC11207 and TIC11304 family both in planta (combined through breeding or molecular stacking) or in a composition or formulation as a biopesticide or combination of biopesticides.

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC11207 or TIC11304 pesticidal protein.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g., from 0.0001% to 0.001% to 0.01% to 1% to 99% by weight of the recombinant polypeptide.

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

EXAMPLES

Example 1

Discovery, Cloning, and Expression of TIC11207 and TIC11304

The TIC11207 pesticidal protein was identified through sequence analysis of the genome of *Paenarthrobacter nitroguajacolicus* strain MDI-0030264. DNA was isolated from MDI-0030264 and sequenced. The assembled sequence was then analyzed bioinformatically. The TIC11207 protein was identified by pfam analysis to hits of ETX_MTX2-type proteins. A homolog to TIC11207, TIC11304 was identified through sequence analysis of the genome of *Paenarthrobacter nitroguajacolicus* species MDI-0030376. A search against patent and public sequences revealed a homolog protein, APG01463 presented in United States patent application publication US20180066277 (SEQ ID NO:42) which is around 80% identical to TIC11207 and around 78% identical to TIC11307. FIG. 1 shows the alignment between TIC11207, TIC11304, and APG01463, wherein identical amino acids are indicated with asterisks below the alignment.

Polymerase chain reaction (PCR) primers were designed to amplify a full-length copy of the coding region for TIC11207 and TIC11304 from total genomic DNA isolated from *Paenarthrobacter nitroguajacolicus* strain MDI-0030264 and MDI-0030376. The PCR amplicons were cloned using methods known in the art into two plasmid constructs: one into an *Escherichia coli* (Ec) expression vector in operable linkage with an Ec expressible promoter and a histidine tag used for protein purification; and the other into a Bt expression vector in operable linkage with a Bt expressible promoter. The coding sequences for the histidine tagged TIC11207-his and TIC11304-his proteins (SEQ ID NOs: 17 and 19) are presented as SEQ ID NOs; 16 and 18, respectively. Preparations of TIC11207 and TIC11304 derived from both Ec and Bt were used in bioassay.

Example 2

TIC11207 Demonstrates Hemipteran Activity and TIC11304 Demonstrates Hemipteran and Lepidopteran Activity in Insect Bioassay The pesticidal proteins TIC11207 and TIC11304 were expressed in recombinant Ec and Bt using the vectors described in Example 1, and the resulting proteins expressed in these systems were assayed for toxicity to various species of Hemiptera, Lepidoptera, and Coleoptera.

TIC11207 was assayed for toxicity to the Lepidopteran insect species Fall armyworm (FAW, *Spodoptera frugiperda*) and the Hemipteran insect species Southern Green Stink Bug (SGSB, *Nezara viridula*), Neotropical Brown Stink Bug (NBSB, *Euschistus heros*), and Western tarnished plant bug (WTP, *Lygus hesperus*). TIC11304 was assayed for toxicity to the Lepidopteran insect species Fall armyworm (FAW, *Spodoptera frugiperda*), Southern armyworm (SAW, *Spodoptera eridania*), and Soybean looper (SBL, *Chrysodeixis includens*); the Hemipteran insect species Southern Green Stink Bug (*Nezara viridula*), Neotropical Brown Stink Bug (*Euschistus heros*), and Western tarnished plant bug (*Lygus hesperus*); and the Coleopteran species Western Corn Rootworm (WCR, *Diabrotica virgifera*). The bioassay results are presented in Table 3 below wherein "+" indicates activity, "−" indicates no activity, and "NT" indicates not tested.

when in a plant cell, using skills known in the art. Transformation vectors used to transform soybean plants comprised a right border sequence derived from *Agrobacterium tumefaciens*; a first transgene cassette for the selection of transformed plant cells using Spectinomycin selection; a second transgene cassette for the expression of TIC11207PL or TIC11304PL comprised a constitutive promoter, operably linked 5' to a leader, operably linked 5' to an intron, operably linked 5' to an artificial coding sequence encoding TIC11207PL or TIC11304PL, which was in turn operably linked 5' to a 3' UTR; and a left border sequence derived from *Agrobacterium tumefaciens*.

Example 4

TIC11207PL Exhibits Activity Against Neotropical Brown Stink Bug (NBSB, *Euschistus heros*) when Expressed in Stably Transformed Soybean Plants A binary plant transformation vector comprising a transgene cassette designed to express TIC11207PL using the coding sequence of SEQ ID NO:3 was cloned using methods known in the art. The resulting vector was used to stably transform soybean plants. The transformed soybean plants were infested with Neotropical Brown Stink Bug (NBSB, *Euschistus heros*) and assayed for activity against NBSB.

Stably transformed $R_0$ soybean plants expressing TIC11207PL with at least one R5.5 pod were infested with NBSB eggs by gluing two egg masses, each comprising approximately 19 eggs per mass in agar on rayon fabric to a complete soybean trifoliate leaf. The plants were then

TABLE 3

Activity of TIC11207 and TIC11304 against Lepidopteran, Coleopteran, and Hemipteran insect species.

| Toxin | Lepidopteran | | | | | Coleopteran | Hemipteran | | |
|---|---|---|---|---|---|---|---|---|---|
| | BCW | CEW | FAW | SAW | SBL | WCR | WTP | SGSB | NBSB |
| TIC11207 | NT | NT | − | NT | NT | NT | + | + | + |
| TIC11304 | − | − | − | + | + | − | + | + | + |

As can be seen from the data presented in Table 3, TIC11207 demonstrated activity against WTP, SGSB, and NBSB. TIC11304 demonstrated activity against SAW, SBL, WTP, SGSB, NBSB.

Example 3

Design of Artificial Coding Sequences for TIC11207PL and TIC11304PL for Use in Expression in Plants Artificial coding sequences SEQ ID NOs: 3, 5, 6, 7, 8, 9, 10, 13, and 15 encoding TIC11207PL and TIC11304PL were designed for expression in a plant cell. The artificial (alternatively referred to as synthetic) sequence was synthesized, according to methods generally described in U.S. Pat. No. 5,500,365, to avoid certain inimical problem sequences such as ATTTA and A/T rich plant polyadenylation sequences, while preserving the amino acid sequence of the native *Bacillus* protein. The amino acid sequence of TIC11207PL and TIC11304PL comprise an additional alanine residue inserted after the initiating methionine of TIC11207 and TIC11304 to improve expression.

The artificial coding sequences encoding TIC11207PL and TIC11304PL were cloned into plant transformation vectors and downstream of and functionally linked to plant promoters for driving expression of the coding sequences covered with an organza fabric bag to prevent escape of the nymphs after hatching. Around 80% of the eggs hatched for each plant. At day 15, the bags with the soybean plants were collected by cutting the stem with hand pruners below the closer of the bag. Around 92% of the bugs were recovered by this method. Living bugs were counted for each $R_0$ event, as well as the instar stage of each nymph. Untransformed control plants were also used in this assay to compare with the plants expressing TIC11207PL. The mean percent survival of NBSB is presented in Table 4 below and shown graphically in FIG. 2.

TABLE 4

Mean percent survival of Neotropical Brown Stink Bug (NBSB, *Euschistus heros*) in stably transformed $R_0$ plants expressing TIC11207PL.

| Toxin | Mean | Standard Error |
|---|---|---|
| Control | 80.77 | 1.71 |
| TIC11207PL | 54.08 | 8.84 |

Figure 3:
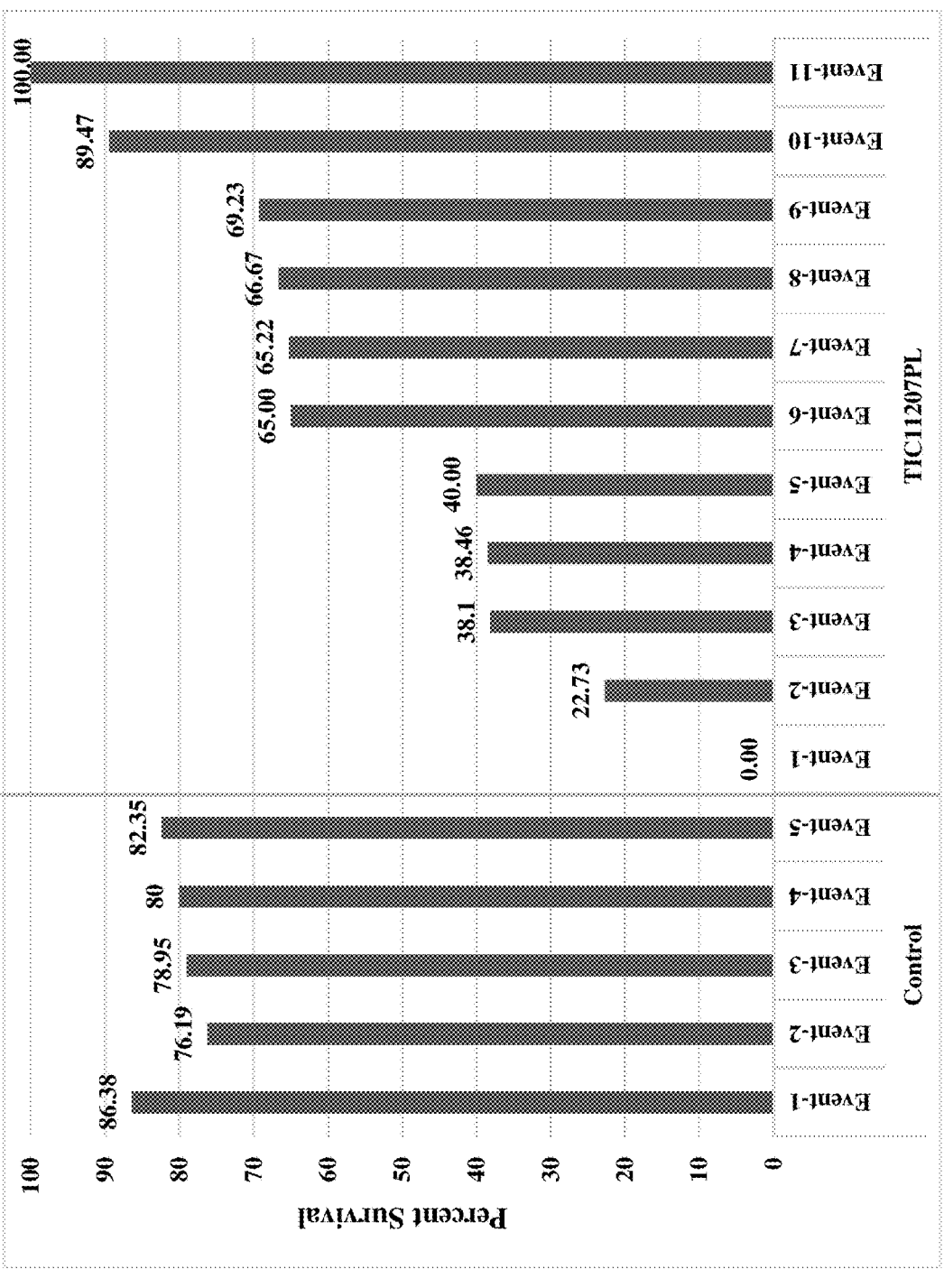
FIG. 3 is a graphical representation of the percent survivorship of Neotropical Brown Stink Bug (*Euschistus heros*) when feeding on stably transformed soybean events expressing the TIC11207PL protein. The control plants are wild-type untransformed soybean plants.

As can be seen in Table 4 and FIG. 2, soybean plants expressing TIC11207PL demonstrated activity against NBSB when compared to the control plants. Table 5 below and FIG. 3 shows the individual events used to calculate the mean for the Control and TIC11207PL percent survivorship.

TABLE 5

Percent survival of Neotropical Brown Stink Bug (NBSB, *Euschistus heros*) in stably transformed $R_0$ plants expressing TIC11207PL.

| Toxin | Event | Percent Survival |
|---|---|---|
| Control | Event-1 | 86.38 |
| | Event-2 | 76.19 |
| | Event-3 | 78.95 |
| | Event-4 | 80.00 |
| | Event-5 | 82.35 |
| TIC11207PL | Event-1 | 0.00 |
| | Event-2 | 22.73 |
| | Event-3 | 38.10 |
| | Event-4 | 38.46 |
| | Event-5 | 40.00 |
| | Event-6 | 65.00 |
| | Event-7 | 65.22 |
| | Event-8 | 66.67 |
| | Event-9 | 69.23 |
| | Event-10 | 89.47 |
| | Event-11 | 100.00 |

As can be seen in Table 5 above and FIG. 3, 5 $R_0$ soybean plants expressing TIC11207PL demonstrated a percent survivorship of NBSB less than 50%.

Soybean plants expressing TIC11207PL demonstrate resistance to Neotropical Brown Stink Bug (*Euschistus heros*).

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

---

What is claimed is:

1. A recombinant nucleic acid molecule comprising a heterologous promoter operably linked to a polynucleotide segment encoding a pesticidal protein or fragment thereof, wherein:

a. said pesticidal protein comprises the amino acid sequence of SEQ ID NOs: 2, 4, 12, 14, 17, or 19; or b. said pesticidal protein comprises an amino acid sequence having at least 95% amino acid sequence identity to SEQ ID NOs: 2, 4, 12, 14, 17, or 19; or c. said polynucleotide segment comprises a polynucleotide having at least 95% sequence identity to the nucleotide sequence of SEQ ID NOs: 1, 3, 5, 6, 7, 8, 9, 10, 11, 13, 15, 16, or 18.

2. The recombinant nucleic acid molecule of claim 1, wherein:

a. said recombinant nucleic acid molecule is expressed in a plant cell to produce a pesticidally effective amount of the pesticidal protein or pesticidal fragment; or b. said recombinant nucleic acid molecule is in operable linkage with a vector, and said vector is selected from the group consisting of a plasmid, phagemid, bacmid, cosmid, and a bacterial or yeast artificial chromosome.

3. The recombinant nucleic acid molecule of claim 1, wherein said recombinant nucleic acid molecule is present within a bacterial host cell selected from the group consisting of: *Agrobacterium, Rhizobium, Bacillus, Brevibacillus, Escherichia, Pseudomonas, Klebsiella, Pantoea, Paenarthrobacter*, and *Erwinia; and/or* wherein the bacterial host cell is selected from the group consisting of *Bacillus cereus* or *Bacillus thuringiensis, Brevibacillus laterosperous*, and *Escherichia coli.*

4. The recombinant nucleic acid of claim 1, wherein said recombinant nucleic acid molecule is present within a plant cell, wherein the plant cell is selected from the group consisting of a dicotyledonous and a monocotyledonous plant cell; or wherein said plant cell is selected from the group consisting of an alfalfa, banana, barley, bean, broccoli, cabbage, brassica, canola, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, corn, sweet gum, sweet potato, switchgrass, tea, tobacco, tomato, triticale, turf grass, watermelon, and wheat plant cell.

5. The recombinant nucleic acid molecule of claim 1, wherein said pesticidal protein exhibits activity against an insect species of the order of Hemiptera or Lepidoptera.

6. The recombinant nucleic acid molecule of claim 5, wherein said insect species is selected from the group consisting of Southern Green Stink Bug (*Nezara viridula*), Neotropical Brown Stink Bug (*Euschistus heros*), Western tarnished plant bug (*Lygus hesperus*) Southern armyworm (*Spodoptera eridania*), and Soybean looper (*Chrysodeixis includens*).

7. A plant comprising the recombinant nucleic acid molecule of claim 1, or a part thereof.

8. The plant of claim 7, wherein said plant is a monocot plant or a dicot plant, or a part thereof; and/or wherein the plant is selected from the group consisting of an alfalfa, banana, barley, bean, broccoli, cabbage, brassica, canola, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, corn, sweet gum, sweet potato, switchgrass, tea, tobacco, tomato, triticale, turf grass, watermelon, and wheat; and/or wherein the part of the plant thereof is a seed, and wherein said seed comprises said recombinant nucleic acid molecule.

9. An insect inhibitory composition comprising the recombinant nucleic acid molecule of claim 1.

10. The insect inhibitory composition of claim 9, further comprising a nucleotide sequence encoding at least one other pesticidal agent that is different from said pesticidal protein; and/or wherein said composition is defined as comprising a plant cell that expresses the pesticidal protein from the recombinant nucleic acid molecule of claim 1.

11. The insect inhibitory composition of claim 10, wherein said at least one other pesticidal agent is selected from the group consisting of an insect inhibitory protein, an insect inhibitory dsRNA molecule, a chemical molecule and an ancillary protein, wherein said at least one other pesticidal agent is toxic to the same pest as the pesticidal protein or pesticidal fragment thereof; and/or wherein said at least one other pesticidal agent exhibits activity against one or more pest species of the orders Hemiptera or Lepidoptera; and/or wherein said at least one other pesticidal protein is selected from the group consisting of a Cry1A, Cry1Ab, Cry1Ac, Cry1A.105, Cry1Ae, Cry1B, Cry1C, Cry1C variants, Cry1D, Cry1D variants, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, TIC4029, TIC4064, TIC13085, TIC13087, VIP3A, VIP3B, VIP3Ab, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI- 225z, AXMI-238, AXMI-270, AXMI-279, AXMI-345, AXMI-335, AXMI-R$_1$ and variants thereof, IP3 and variants thereof, DIG-3, DIG-5, DIG-10, DIG-657, DIG-11 protein, IPD102Aa and homologs thereof, IPD110Aa and homologs thereof, TIC868, Cry1Da1_7, BCW003, TIC1100, TIC867, TIC867_23, TIC6757.TIC7641, IPD072Aa and homologs thereof, TIC5290, TIC3668, TIC3669, TIC3670, IPD103 and homologs thereof, PIP-50 and PIP-65 and homologs thereof, PIP-83 and homologs thereof, a fern protein toxic to hemiptera species, and Cry1B.34.

12. A commodity product produced from the plant of claim 7, or part thereof, wherein the commodity product comprises a detectable amount of said recombinant nucleic acid molecule.

13. The commodity product of claim 12, selected from the group consisting of flakes, cakes, starch, jams, jellies, marmalades, processed seed, oil, lint, fiber, paper, meal, and flour.

14. A method of producing progeny seed comprising the recombinant nucleic acid molecule of claim 1, the method comprising:

a. planting a first seed comprising the recombinant nucleic acid molecule;

b. growing a plant from the seed of step a; and c. harvesting the progeny seed from the plants, wherein said harvested seed comprises said recombinant nucleic acid molecule.

15. A plant resistant to insect infestation, wherein the cells of said plant comprise the recombinant nucleic acid molecule of claim 1.

16. A method of detecting the presence of the recombinant nucleic acid molecule of claim 1 in a sample comprising plant genomic DNA, comprising:

a. contacting said sample with a nucleic acid probe that hybridizes under stringent hybridization conditions with genomic DNA from a plant comprising the recombinant nucleic acid molecule of claim 1, and does not hybridize under such hybridization conditions with genomic DNA from an otherwise isogenic plant that does not comprise the recombinant nucleic acid molecule of claim 1;

b. subjecting said sample and said probe to stringent hybridization conditions; and c. detecting hybridization of said nucleic acid probe with said recombinant nucleic acid molecule.

17. A pesticidally effective amount of a protein encoded by the recombinant nucleic acid molecule of claim 1.

* * * * *

SEQUENCE LISTING

```
Sequence total quantity: 20
SEQ ID NO: 1              moltype = DNA   length = 975
FEATURE                   Location/Qualifiers
source                    1..975
                          mol_type = genomic DNA
                          note = A nucleic acid sequence encoding a TIC11207
                           pesticidal protein obtained from Paenarthrobacter
                           nitroguajacolicus strain MDI-0030264.
                          organism = Paenarthrobacter nitroguajacolicus
SEQUENCE: 1
atgtctgact caccaggtat caacatctcc atggtcgcag cacccaccca agcaggatgc   60
tcgattggcg ccgtcggcaa gatggtaaaa ccaattcagg atagtgacgt cccatatttc   120
tttccgaatg gcgtagtcag tgctatgcag caccactatc cggggtaccg catcggcggg   180
gcttggctcc acgaccccac cccgggcgcc ccatattctg acatgtttgc ctactacaag   240
gactggcctg ggggcccgac tccagtaact gtcatctaca agcccgtatc tgcgagggtc   300
gtctccatgt cccccgaggc tgcctacaag tacgaccagg actttataaa tgacagctct   360
gtaggggcaa cgtttaattg ctccctcaca cagtcggtaa ccaactcagt ctcaactacc   420
aaaactgagg gggacagcct gaaggtcggt cagaaattga cgtatggtgt cgaattcctc   480
ggctccggtg ttaagggtga gaccagcgcc gagtacacac atacttgggg tacctcggat   540
acgaacacga cgaccgtcac agtcggtacc gccagtggaa tatcagtttt cctagaacca   600
gggcagaagg tgacagccga gcttaccgcc tcccgcagta agctcgttgt cgaagtgacc   660
tacgatgtca ccctggatgg aagtgtcgtc ttcactacgc ccaactggga tttgggcggg   720
caccgcgatc actggttctg ggttggggagc cttctggatg atgccaatgg cgggaatccc   780
ccgaactcct ctgtaggcat caggcgcaca gagcagatca ctttggattt ctatgcaaac   840
ggagtaacta ggttgctcga taacaccggc aaggtgctcc tcaccgtaaa ggacggacac   900
gggcgggcag aagcgaagga tgaagagtcc ctcacgcttg aagcgttgcg tgaggcagcc   960
tcacaagggg cctag                                                   975

SEQ ID NO: 2              moltype = AA   length = 324
FEATURE                   Location/Qualifiers
source                    1..324
                          mol_type = protein
                          note = The amino acid sequence of the TIC11207 pesticidal
                           protein encoded by the sequence set forth in SEQ ID NO:1.
                          organism = Paenarthrobacter nitroguajacolicus
SEQUENCE: 2
MSDSPGINIS MVAAPTQAGC SIGAVGKMVK PIQDSDVPYF FPNGVVSAMQ HHYPGYRIGG   60
AWLHDPTPGA PYSDMFAYYK DWPGGPTPVT VIYKPVSARV VSMSPEAAYK YDQDFINDSS   120
VGATFNCSLT QSVTNSVSTT KTEGDSLKVG QKLTYGVEFL GSGVKGETSA EYTHTWGTSD   180
TNTTTVTVGT ASGISVFLEP GQKVTAELTA SRSKLVVEVT YDVTLDGSVV FTTPNWDLGG   240
HRDHWFWVGS LLDDANGGNP PNSSVGIRRT EQITLDFYAN GVTRLLDNTG KVLLTVKDGH   300
GRAEAKDEES LTLEALREAA SQGA                                          324

SEQ ID NO: 3              moltype = DNA   length = 978
FEATURE                   Location/Qualifiers
```

-continued

```
source              1..978
                    mol_type = other DNA
                    note = The amino acid sequence of the TIC11207 pesticidal
                     protein encoded by the sequence set forth in SEQ ID NO:1.
                    organism = synthetic construct
SEQUENCE: 3
atggcgtcgg atagccccgg cattaacatc agcatggtag cagctcctac tcaagccggt  60
tgttctattg gggctgtggg aaagatggtc aagcccattc aagatagtga tgtgccgtac  120
ttctttccta atggcgtcgt aagcgcgatg caacatcatt acccaggcta ccgtattggc  180
ggggcatggc tccatgaccc gacaccggga gcaccctata gcgatatgtt cgcttattac  240
aaagattggc caggcggtcc gacaccggtc acggtcatat acaaaccgt atctgcgaga  300
gtcgtatcca tgagtcccga ggccgcctac aaatacgacc aagactttat caacgactca  360
tcagtgggtg cgaccttcaa ctgctcattg acgcaatcgg tgaccaatag cgtttcaaca  420
actaagactg agggagactc cttaaaagtg ggccagaagc taacttacgg agtcgagttc  480
ttgggatcgg gcgtcaaagg tgaaaccagc gcggagtaca cgcatacctg gggtacgagt  540
gacacaaaca ctaccacagt cacagtgggc actgcgtccg ggatctcagt attccttgag  600
ccaggccaga aggtgaccgc tgagcttacc gctagtcgtt ccaaattggt agtggaagta  660
acatacgatg taacgctaga tggatcggtc gtgttcacta caccgaactg ggatctgggt  720
ggtcatcgag accactggtt ctgggttggc tccctactcg atgatgcgaa cggcggcaat  780
cctcctaatt ctagtgtcgg catacgaagg acggagcaaa ttactctgga cttctatgca  840
aacggagtaa cgaggctgtt ggacaacacg gggaaagtgt tgctaacggt gaaagatggt  900
cacggtagag ccgaggcaaa ggacgaggag agcctgacgt tggaagcgtt gcgtgaggct  960
gctagtcaag gcgcgtga                                                 978

SEQ ID NO: 4           moltype = AA   length = 325
FEATURE                Location/Qualifiers
source                 1..325
                       mol_type = protein
                       note = The amino acid sequence of the TIC11207PL pesticidal
                        protein encoded by SEQ ID NOs:3, 5, 6, 7, 8, 9, and 10,
                        wherein an additional alanine residue is inserted
                        immediately following the initiating methionine.
                       organism = synthetic construct
SEQUENCE: 4
MASDSPGINI SMVAAPTQAG CSIGAVGKMV KPIQDSDVPY FFPNGVVSAM QHHYPGYRIG  60
GAWLHDPTPG APYSDMFAYY KDWPGGPTPV TVIYKPVSAR VVSMSPEAAY KYDQDFINDS  120
SVGATFNCSL TQSVTNSVST TKTEGDSLKV GQKLTYGVEF LGSGVKGETS AEYTHTWGTS  180
DTNTTTVTVG TASGISVFLE PGQKVTAELT ASRSKLVVEV TYDVTLDGSV VFTTPNWDLG  240
GHRDHWFWVG SLLDDANGGN PPNSSVGIRR TEQITLDFYA NGVTRLLDNT GKVLLTVKDG  300
HGRAEAKDEE SLTLEALREA ASQGA                                        325

SEQ ID NO: 5           moltype = DNA   length = 978
FEATURE                Location/Qualifiers
source                 1..978
                       mol_type = other DNA
                       note = A synthetic coding sequence, TIC11207PL-2 encoding a
                        TIC11207PL pesticidal protein and capable of use in a
                        plant cell, wherein an additional codon encoding an
                        alanine residue is inserted immediately following the
                        initiating methionine codon.
                       organism = synthetic construct
SEQUENCE: 5
atggcgtccg atagtccggg gattaacatt agcatggttg ccgccctac gcaagccggt  60
tgctccattg gtgccgtagg aaagatggtt aagcctatac aagattctga tgttccgtac  120
ttctttccga atggagtcgt atcagcaatg caacatcact atccggggtta tcgaattgga  180
ggtgcatggc ttcatgaccc tacaccgggt gctccttatt ccgatatgtt cgcttattac  240
aaagattggc caggagggcc tacgcctgtt accgtgatct acaaaccagt ctcagcccga  300
gtcgtctcaa tgtcgccaga agctgcctac aaatacgacc aagacttcat taacgattct  360
agcgtgggag caactttcaa ctgttcactt acccaatcag tgacaaattc cgtatctacg  420
actaaaactg agggagactc cctgaaagtc ggccagaaac ttacttatgg tgttgagttc  480
ctgggatctg gagtcaaagg cgaaacctcg gctgagtaca cacatacctg gggaactagc  540
gatacgaaca caacaaccgt tactgttggt actgcctctg gaatttcggt attccttgaa  600
cctggccaga aggtcactgc tgaactgaca gcttctcgat ccaaacttgt cgttgaagtg  660
acctatgatg tgaccttgga cggctcggta gtctttacta cgcccaactg ggatctggga  720
gggcatcggg atcactggtt ctgggtggga tcgctcttgg atgacgccaa cggagggaat  780
ccaccgaact caagtgtcgg gattcggagg acgaacaaa tcacccttga cttttacgcg  840
aatggtgtta cgcgactgtt ggacaacacc ggcaaagtgc ttctcacagt gaaagatggt  900
catggacgcg cagaggctaa agatgaggag agtttgactt tggaggcttt acgggaagct  960
gcatctcaag gagcttaa                                                978

SEQ ID NO: 6           moltype = DNA   length = 978
FEATURE                Location/Qualifiers
source                 1..978
                       mol_type = other DNA
                       note = A synthetic coding sequence, TIC11207PL-2 encoding a
                        TIC11207PL pesticidal protein and capable of use in a
                        plant cell, wherein an additional codon encoding an
                        alanine residue is inserted immediately following the
                        initiating methionine codon.
```

-continued

```
                              organism = synthetic construct
SEQUENCE: 6
atggcgtcgg atagtcctgg catcaatatc agcatggtag ccgctcccac ccaagctggg    60
tgctcaattg gggctgttgg gaaaatggtg aagcctacac aagactccga cgtaccatac   120
ttcttcccca atggcgtcgt cagtgcgatg caacaccatt accctggtta tcgaatcggt   180
ggtgcatggc tacatgatcc cacgccaggc gcaccttatt ctgatatgtt cgcctactac   240
aaggactggc ctggtggacc cacacccgtt actgtcatat acaaacctgt gtcagcgaga   300
gttgttagca tgtctccgga agccgcctac aaatacgatc aagactttat caatgattca   360
tctgtgggag ctacgttcaa ttgctctttg acccagagtg taactaatag cgtgtccacc   420
actaaaacgg aaggcgattc cttaaaagta ggtcaaaagc tgacttatgg ggtagagttc   480
ttgggctccg gcgtcaaagg agaaacgtct gctgagtaca cgcatacttg gggtacatct   540
gacacgaata cgactactgt tacggttggc acagccagcg gaatcagcgt gttccttgag   600
cctggccaga aggttactgc cgagctaacc gcttcccgga gcaagctagt tgtggaagtt   660
acttatgacg ttacgcttga cggaagcgta gtattcacta caccaattg ggatttggga   720
ggtcaccgag atcactggtt ctgggttggg tcattgctag atgatgcaaa tggtggaaac   780
ccaccgaata gctctgtcgg cataagacgt actgaacaaa ttactctcga cttctatgca   840
aacggggtta cgcgactact tgacaatacg gggaaagtgc tattaaccgt caaagacgga   900
catggtagag ccgaagctaa agatgaggag agtttgactc tggaagcact tcgggaggct   960
gccagccagg gagcataa                                                 978

SEQ ID NO: 7                  moltype = DNA  length = 978
FEATURE                       Location/Qualifiers
source                        1..978
                              mol_type = other DNA
                              note = A synthetic coding sequence, TIC11207PL-4 encoding a
                              TIC11207PL pesticidal protein and capable of use in a
                              plant cell, wherein an additional codon encoding an
                              alanine residue is inserted immediately following the
                              initiating methionine codon.
                              organism = synthetic construct
SEQUENCE: 7
atggcgtcag atagcccagg gattaacatc tcgatggtag cagcacctac ccaagcggga    60
tgctctattg gcgcggttgg gaagatggtg aaacctattc aagactccga cgtaccctac   120
ttctttccca atggagttgt cagcgctatg caacatcatt atccgggcta tcggattggt   180
ggagcatggt tgcacgaccc cacgccaggg gcacctatt cggatatgtt cgcatattac   240
aaaagattggc ccggcggacc aacccagt actgtcatct acaagccagt ctctgccaga   300
gtcgtttcca tgtctcccga ggccgcgtac aaatacgacc aagacttcat taacgactca   360
tccgtcggcg cgacgttcaa ttgttccttg acacaaagcg tgactaattc tgtctctact   420
accaaaacgg aaggagattc acttaaagtt ggacaaaagt tgacgtacgg tgtggagttc   480
ttggggtctg gcgtgaaagg agagacttct gctgagtaca cgcacacatg gggcacatcg   540
gatacaaata cgaccacagt taccgtagga acggctagtg gtatttcggt gttcttagaa   600
cctggccaga aggttaccgc cgagttgacc gcttctcgat ccaaattggt ggttgaagta   660
acctatgatg ttacactcga cgggagcgtt gtctttacaa caccaaattg ggatctgggc   720
gggcatcgtg accactggtt ctgggttgga tcactattgg atgatgcgaa tggcgggaat   780
ccaccaaact catcagttgg tattcgccgg actgaacaaa ttactttgga cttctacgca   840
aatgcgtaa ctcgactgtt ggacaacacg gggaaagtcc tattaactgt caaagatgga   900
catggtagag ctgaggccaa agatgaggaa agccttacct tagaggcact tcgtgaagct   960
gcttcacaag gagcttaa                                                 978

SEQ ID NO: 8                  moltype = DNA  length = 978
FEATURE                       Location/Qualifiers
source                        1..978
                              mol_type = other DNA
                              note = A synthetic coding sequence, TIC11207PL-5 encoding a
                              TIC11207PL pesticidal protein and capable of use in a
                              plant cell, wherein an additional codon encoding an
                              alanine residue is inserted immediately following the
                              initiating methionine codon.
                              organism = synthetic construct
SEQUENCE: 8
atggcgtctg attcacccgg catcaatatc tctatggtcg cagctccaac gcaagctgga    60
tgttctattg gagccgtagg aaagatggtc aagccaatcc aagattctga tgtgccctac   120
ttctttccca atggagtcgt gtctgcaatg caacatcatt accctggcta ccggatcggt   180
ggtgcatggc tgcatgatcc aacgcccggt gctccatact ctgatatgtt cgcatattac   240
aaagactggc cggcggggcc aacgcccgtc actgtcatat acaagccagt gtctgctaga   300
gtagtttcaa tgagtccgga ggctgcctac aaatacgacc aagactttat caacgatagc   360
tctgtcgggg caacgttcaa ttgttcctta acgcaatccg tcactaattc tgtttcaaca   420
acaaagaccg aaggggattc cttaaaagtg ggtcaaaagt tgacgtatgg tgtcgagttc   480
ctgggttctg gggtcaaggg tgaaacatct gctgagtaca cacatacctg gggaacttac   540
gataccaata ccactacggt cacagtcggc acagcgtcgg gtattagcgt attcttggag   600
cctggccaga aggttacggc tgaactgaca gcttctcgta gtaagctcgt ggtagaggtt   660
acctacgatg tgacactaga cggaagcgtc gttttcacaa cccctaattg ggatttgggt   720
ggtcatcgtg accactggtt ctgggtgggc tctctgttag acgatgcaaa tggagggaat   780
ccacctaatt cctctgttgg aatacggaga actgagcaaa tcactctaga cttctatgct   840
aatggtgtaa caaggctact tgacaatacc ggaaaagttc tgttgacggt caaagatggt   900
catggccgtg ccgaagccaa agatgaggaa tcgttgaccc ttgaggcgct ccgtgaggcg   960
gcatctcaag gtgcttaa                                                 978

SEQ ID NO: 9                  moltype = DNA  length = 978
```

```
FEATURE                   Location/Qualifiers
source                    1..978
                          mol_type = other DNA
                          note = A synthetic coding sequence, TIC11207PL-6 encoding a
                           TIC11207PL pesticidal protein and capable of use in a
                           plant cell, wherein an additional codon encoding an
                           alanine residue is inserted immediately following the
                           initiating methionine codon.
                          organism = synthetic construct
SEQUENCE: 9
atggcgagtg actccctgg catcaatatc tcaatggttg ctgctcctac ccaggctgga   60
tgttcgattg gagcagtcgg caaaatggtt aaaccgatac aagatagtga tgtaccctac   120
ttctttccaa atggagttgt ctccgcgatg caacaccact acccaggata ccgtattggc   180
ggagcgtggc tgcatgaccc aactcccggc gctccctatt ctgatatgtt cgcatattac   240
aaggactggc cgggcggacc tacccctgtc actgttatct acaaaccagt gtctgcaaga   300
gtagtgtcaa tgtccccaga agctgcgtac aaatacgatc aagacttcat caatgattcg   360
tcagttggcg caaccttcaa ctgttcgcta actcaatcag ttaccaatag tgtgtcaact   420
acaaagactg agggagattc acttaaagtg ggtcaaaagc tgacgtatgg tgttgagttc   480
ttggggtctg gcgtgaaagg agaaacctct gctgagtaca cacacacatg gggcacgagc   540
gataccaaca ctacgactgt aactgtcgga acggcgtctg gaatatccgt ctttctcgaa   600
cctggccaga aggtcacagc cgaattgaca gcttctcgga gcaaactcgt cgttgaagtc   660
acttatgacg tgacattgga tggttccgtc gtgtttacga caccaaactg ggatcttgga   720
ggacaccggg atcactggtt ctgggtcggc tcgctgttag acgatgcaaa cggcggcaat   780
cctcctaact cctctgtcgg aatacgtcgt actgagcaaa ttactctgga cttttacgcc   840
aacggtgtta cacgccttct cgataacact ggaaaggttc tactgacggt caaagatggt   900
catggtagag ctgaggctaa ggatgaggag agtttaactt tggaggcttt acgcgaagcc   960
gccagtcaag gtgcttaa                                                 978

SEQ ID NO: 10            moltype = DNA   length = 978
FEATURE                  Location/Qualifiers
source                   1..978
                         mol_type = other DNA
                         note = A synthetic coding sequence, TIC11207PL-7 encoding a
                          TIC11207PL pesticidal protein and capable of use in a
                          plant cell, wherein an additional codon encoding an
                          alanine residue is inserted immediately following the
                          initiating methionine codon.
                         organism = synthetic construct
SEQUENCE: 10
atggcgagcg attctcctgg cattaacatt agcatggtag ctgcgccaac acaagccgga   60
tgttcaattg gtgctgttgg caaaatggtt aagccgattc aagatagtga cgttccatac   120
ttctttccca atggagtagt gtctgcaatg caacatcatt acccaggata ccgtattggc   180
ggagcgtggt tgcatgaccc cacacctggt gctccttatt ctgatatgtt cgcttattac   240
aaagattggc ccggaggccc cacccccggtc acagtcatat acaaacctgt ttccgcaagg   300
gtcgtgtcta tgagtcccga agctgcctac aaatacgatc aagactttat caacgacagc   360
tctgttgggg ccacgttcaa ttgctcccta actcagtccg ttactaattc tgttagcacg   420
acgaagaccg aaggagattc acttaaagtc gggcaaaagc tcacctatgg ggtggagttc   480
ctcgggtctg gtgtcaaggg cgaaacttcg gctgagtaca cacacacctg gggaacttcg   540
gacacgaaca caactacggt gaccgtgggc accgcaagcg gtatatccgt tttccttgaa   600
cctggccaga aggttacggc tgaactaact gcttctcgat ctaagttggt cgtagaggtt   660
acttatgacg tgacattgga cggtagtgtc gtctttacaa cccctaactg ggatctggat   720
ggtcatcgtg accactggtt ctgggttgga tctctgctag atgatgcaaa tggcgggaat   780
cctcctaatt cgagtgtcgg gattcgtaga actgagcaaa tcaccctcga cttctatgcg   840
aatggcgtta ctagactact tgacaacacc ggcaaggttc tgttgaccgt gaaagatggt   900
catggtagag ctgaggctaa agatgaggaa tccttgaccc tggaagctct gcgtgaagct   960
gcgagtcaag gtgcataa                                                 978

SEQ ID NO: 11            moltype = DNA   length = 975
FEATURE                  Location/Qualifiers
source                   1..975
                         mol_type = genomic DNA
                         note = A nucleic acid sequence encoding a TIC11304
                          pesticidal protein obtained from Paenarthrobacter
                          nitroguajacolicus strain MDI-0030376.
                         organism = Paenarthrobacter nitroguajacolicus
SEQUENCE: 11
atgtctgact caccaggtat caacatctcc atggtcgcag cacccacccc agcaggatgc   60
tcgattggcg ccgtcggcaa gatggttagg ccgattcagg atagtgacgt cccatatttc   120
tttccgaatg gcgtagtcag tgctatgcag catcactatc cgggctacaa catcggcggg   180
gcctggcttc acgaccccac cccgggcgcc ccatattccg acatgtttgc ctactataag   240
gactggcctg ggggtccaac cccagtaact gtcatctaca gcccgtatc tgcgagggtc   300
gtctccatgt cccccgaggc tgcctacaag tacgaccagg actttataaa tgaaagctct   360
gtaggggcaa cgtttaattg ctccctcaca caatcggtaa ccaactcagt ctcaactacc   420
aaaactgagg gggacgcct gaaggtcggt cagaaattga cgtatggtgt tgaattcctc   480
ggctccggcg ttaagggtga aaccagcgcc gagtacacac atacttgggg tacctcggat   540
acgaacacga cgaccgtcac cgtcggtacc gccagtggaa tatcagtgtt cctagaacca   600
gggcagaagg tgacagccga gcttacggcc tcccgcagca agctcgttgt cgaagtgacc   660
tacgatgtca ccctggacgg aagtgtcgtc ttcactacac ccaactggga tttgggcgga   720
catcgcgatc actggttctg ggtgggcagc cttttagatg atgccaatgg cgggaatccc   780
```

```
ccgaactcct ccgtaggcat caggcgcacg gagcagatca ctttggattt ctatgcaaac  840
ggagtaacta ggctgctcga taacaccggc aaggtgctcc tcaccgtaga gggcggtcgc  900
gggcaggcag aagcgaagga tgaaaagtcc ttcacgcttg aggccttgcg agaggcagct  960
tccctagggg cctaa                                                    975

SEQ ID NO: 12            moltype = AA  length = 324
FEATURE                  Location/Qualifiers
source                   1..324
                         mol_type = protein
                         note = The amino acid sequence of the TIC11304 pesticidal
                          protein encoded by the sequence set forth in SEQ ID NO:11.
                         organism = Paenarthrobacter nitroguajacolicus
SEQUENCE: 12
MSDSPGINIS MVAAPTPAGC SIGAVGKMVR PIQDSDVPYF FPNGVVSAMQ HHYPGYNIGG  60
AWLHDPTPGA PYSDMFAYYK DWPGGPTPVT VIYKPVSARV VSMSPEAAYK YDQDFINESS  120
VGATFNCSLT QSVTNSVSTT KTEGDSLKVG QKLTYGVEFL GSGVKGETSA EYTHTWGTSD  180
TNTTTVTVGT ASGISVFLEP GQKVTAELTA SRSKLVVEVT YDVTLDGSVV FTTPNWDLGG  240
HRDHWFWVGS LLDDANGGNP PNSSVGIRRT EQITLDFYAN GVTRLLDNTG KVLLTVEGGR  300
GQAEAKDEKS FTLEALREAA SLGA                                         324

SEQ ID NO: 13            moltype = DNA  length = 978
FEATURE                  Location/Qualifiers
source                   1..978
                         mol_type = other DNA
                         note = A synthetic coding sequence, TIC11304PL-1 encoding a
                          TIC1304PL pesticidal protein and capable of use in a plant
                          cell, wherein an additional codon encoding an alanine
                          residue is inserted immediately following the initiating
                          methionine codon.
                         organism = synthetic construct
SEQUENCE: 13
atggcttcgg actcaccggg cattaacatc agtatggttg ccgccccgac gcccgctggc  60
tgttccattg gtgccgttgg caagatggtc cggcccatcc aagactccga tgtcccatac  120
ttcttcccca atggtgtcgt gtccgcgatg caactcact atcctggcta caacattgga  180
ggagcatggt tacacgatcc cacacctgga gcaccatatt cggatatgtt cgcctattac  240
aaggactggc caggaggccc cacgcccgta accgtaatct acaagccagt atctgcgagg  300
gtagtgtcca tgtctcctga ggccgcctac aaatacgatc aagacttcat taacgagtca  360
tcagtcgggg ccactttcaa ctgctccttg acacaatcag ttacgaatag cgtaagcacc  420
actaagacgg agggagaattc tctaaaagtt ggacaaaagt tgacgtacgg agtggagttc  480
ttgggctccg gagtgaaagg agagacgtca gccgagtaca ctcatacttg gggcacgtcc  540
gacacaaata cgaccacagt cactgtcgga accgcatcgg gcataagcgt attcctggag  600
cctggacaaa aggtgaccgc tgagttgacc gcgagccgca gcaaattggt agtggaagtc  660
acctacgacg ttactcttga cggctctgtg gtgtttacaa cccctaattg ggatcttgga  720
ggtcaccgag accactggtt ctgggtcgga tcattactag atgacgctaa cggaggaaat  780
ccgcctaact cctccgtagg gataaggaga accgagcaaa ttccctcga cttctatgct  840
aacgcgtta ctcgtttgct tgataacact ggcaaggtct tgctcacagt cgaaggaggt  900
cgcggccaag cggaggcaaa ggacgaaaag tctttcacat tggaagccct tcgagaagcc  960
gcctcattgg gagcatga                                                978

SEQ ID NO: 14            moltype = AA  length = 325
FEATURE                  Location/Qualifiers
source                   1..325
                         mol_type = protein
                         note = The amino acid sequence of the TIC11304PL pesticidal
                          protein encoded by SEQ ID NOs:13 and 15, wherein an
                          additional alanine residue is inserted immediately
                          following the initiating methionine.
                         organism = synthetic construct
SEQUENCE: 14
MASDSPGINI SMVAAPTPAG CSIGAVGKMV RPIQDSDVPY FFPNGVVSAM QHHYPGYNIG  60
GAWLHDPTPG APYSDMFAYY KDWPGGPTPV TVIYKPVSAR VVSMSPEAAY KYDQDFINES  120
SVGATFNCSL TQSVTNSVST TKTEGDSLKV GQKLTYGVEF LGSGVKGETS AEYTHTWGTS  180
DTNTTTVTVG TASGISVFLE PGQKVTAELT ASRSKLVVEV TYDVTLDGSV VFTTPNWDLG  240
GHRDHWFWVG SLLDDANGGN PPNSSVGIRR TEQITLDFYA NGVTRLLDNT GKVLLTVEGG  300
RGQAEAKDEK SFTLEALREA ASLGA                                        325

SEQ ID NO: 15            moltype = DNA  length = 978
FEATURE                  Location/Qualifiers
source                   1..978
                         mol_type = other DNA
                         note = A synthetic coding sequence, TIC11304PL-2 encoding a
                          TIC11304PL pesticidal protein and capable of use in a
                          plant cell, wherein an additional codon encoding an
                          alanine residue is inserted immediately following the
                          initiating methionine codon.
                         organism = synthetic construct
SEQUENCE: 15
atggcttcgg actcaccggg cattaacatc agtatggttg ccgccccgac gcccgctggc  60
tgttccattg gtgccgttgg caagatggtc cggcccatcc aagactccga tgtcccatac  120
```

-continued

```
ttcttcccca atggtgtcgt gtccgcgatg caacatcact atcctggcta caacattgga  180
ggagcatggt tacacgatcc cacacctgga gcaccatatt cggatatgtt cgcctattac  240
aaggactggc caggaggccc cacgcccgta accgtaatct acaagccagt atctgcgagg  300
gtagtgtcca tgtctcctga ggccgcctac aaatacgatc aagacttcat taacgagtca  360
tcagtcgggg ccactttcaa ctgctccttg acacaatcga ttacgaatag cgtaagcacc  420
actaagacgg agggagattc tctaaaagtt ggacaaaagt tgacgtacgg agtggagttc  480
ttgggctccg gagtgaaagg agagacgtca gccgagtaca ctcatacttg gggcacgtcc  540
gacacaaata cgaccacagt cactgtcgga accgcatcgg gcataagcgt attcctggag  600
cctggacaaa aggtgaccgc tgagttgacc gcgagccgca gcaaattggt agtggaagtc  660
acctacgacg ttactcttga cggctctgtg gtgtttacaa cccctaattg ggatcttgga  720
ggtcaccgag accactggtt ctgggtcgga tcattactag atgacgctaa cggaggaaat  780
ccgcctaact cctccgtagg gataaggaga accgagcaaa ttacccttga cttctatgct  840
aacggcgtta ctcgtttgct tgataacact ggcaaggtct tgctcacagt cgaaggaggt  900
cgcggccaag cggaggcaaa ggacgaaaag tctttcacat tggaagccct tcgagaagcc  960
gcctcattgg gagcatga                                                 978
```

SEQ ID NO: 16          moltype = DNA   length = 993
FEATURE                Location/Qualifiers
source                 1..993
                       mol_type = other DNA
                       note = A nucleic acid sequence encoding TIC11207 pesticidal
                        protein with a Histidine tag operably linked to the 3'
                        end, herein referred to asTIC11207-His.
                       organism = synthetic construct SEQUENCE: 16
```
atgtctgact caccaggtat caacatctcc atggtcgcag cacccaccca agcaggatgc  60
tcgattggcg ccgtcggcaa gatggtaaaa ccaattcagg atagtgacgt cccatatttc  120
tttccgaatg gcgtagtcag tgctatgcag caccactatc cggggtaccg catcggcggg  180
gcttggctcc acgaccccac cccgggcgcc ccatattctg acatgtttgc ctactacaag  240
gactggccgg gggcccgac tccagtaact gtcatctaca agcccgtatc tgcgagggtc  300
gtctccatgt cccccgaggc tgcctacaag tacgaccagg actttataaa tgacagctct  360
gtaggggcaa cgtttaattg ctccctcaca cagtcggtaa ccaactcagt ctcaactacc  420
aaaactgagg gggacagcct gaaggtcggt cagaaattga cgtatggtgt cgaattcctc  480
ggctccggtg ttaagggtga gaccagcgcc gagtacacac atacttgggg tacctcggat  540
acgaacacga cgaccgtcac agtcggtacc gccagtggaa tatcagtttt cctagaacca  600
gggcagaagg tgacagccga gcttaccgcc tcccgcagta agctcgttgt cgaagtgacc  660
tacgatgtca ccctggatgg aagtgtcgtc ttcactacgc ccaactggga tttgggcggg  720
caccgcgatc actggttctg ggttgggagc cttctggatg atgccaatgg cgggaatccc  780
ccgaactcct ctgtaggcat caggcgcaca gagcagatca ctttggattt ctatgcaaac  840
ggagtaacta ggttgctcga taacaccggc aaggtgctcc tcaccgtaaa ggacggacac  900
gggcggggcag aagcgaagga tgaagagtcc ctcacgcttg aagcgttgcg tgaggcagcc  960
tcacaagggg cccaccatca tcaccatcac tag                                993
```

SEQ ID NO: 17          moltype = AA   length = 330
FEATURE                Location/Qualifiers
source                 1..330
                       mol_type = protein
                       note = The amino acid sequence of the TIC11207-His protein
                        encoded by SEQ ID NO:16.
                       organism = synthetic construct SEQUENCE: 17
```
MSDSPGINIS MVAAPTQAGC SIGAVGKMVK PIQDSDVPYF FPNGVVSAMQ HHYPGYRIGG  60
AWLHDPTPGA PYSDMFAYYK DWPGGPTPVT VIYKPVSARV VSMSPEAAYK YDQDFINDSS  120
VGATFNCSLT QSVTNSVSTT KTEGDSLKVG QKLTYGVEFL GSGVKGETSA EYTHTWGTSD  180
TNTTTVTVGT ASGISVFLEP GQKVTAELTA SRSKLVVEVT YDVTLDGSVV FTTPNWDLGG  240
HRDHWFWVGS LLDDANGGNP PNSSVGIRRT EQITLDFYAN GVTRLLDNTG KVLLTVKDGH  300
GRAEAKDEES LTLEALREAA SQGAHHHHHH                                     330
```

SEQ ID NO: 18          moltype = DNA   length = 993
FEATURE                Location/Qualifiers
source                 1..993
                       mol_type = other DNA
                       note = A nucleic acid sequence encoding TIC11304 pesticidal
                        protein with a Histidine tag operably linked to the 3'
                        end, herein referred to as TIC11304-His.
                       organism = synthetic construct SEQUENCE: 18
```
atgtctgact caccaggtat caacatctcc atggtcgcag cacccacccc agcaggatgc  60
tcgattggcg ccgtcggcaa gatggttagg ccgattcagg atagtgacgt cccatatttc  120
tttccgaatg gcgtagtcag tgctatgcag catcactatc cgggctacaa catcggcggg  180
gcctggcttc acgaccccac cccgggcgcc ccatattccg acatgtttgc ctactataag  240
gactggcctg gggtccaac cccagtaact gtcatctaca agcccgtatc tgcgagggtc  300
gtctccatgt cccccgaggc tgcctacaag tacgaccagg actttataaa tgaaagctct  360
gtaggggcaa cgtttaattg ctccctcaca caatcggtaa ccaactcagt ctcaactacc  420
aaaactgagg gggacagcct gaaggtcggt cagaaattga cgtatggtgt tgaattcctc  480
ggctccggcg ttaagggtga aaccagcgcc gagtacacac atacttgggg tacctcggat  540
acgaacacga cgaccgtcac cgtcggtacc gccagtggaa tatcagtgtt cctagaacca  600
gggcagaagg tgacagccga gcttacgccc tcccgcagca agctcgttgt cgaagtgacc  660
tacgatgtca ccctggacgg aagtgtcgtc ttcactacac ccaactggga tttgggcgga  720
```

-continued

```
catcgcgatc actggttctg ggtgggcagc cttttagatg atgccaatgg cgggaatccc 780
ccgaactcct ccgtaggcat caggcgcacg gagcagatca ctttggattt ctatgcaaac 840
ggagtaacta ggctgctcga taacaccggc aaggtgctcc tcaccgtaga gggcggtcgc 900
gggcaggcag aagcgaagga tgaaaagtcc ttcacgcttg aggccttgcg agaggcagct 960
tccctagggg cccaccatca tcaccatcac tag                               993

SEQ ID NO: 19            moltype = AA  length = 330
FEATURE                 Location/Qualifiers
source                  1..330
                        mol_type = protein
                        note = The amino acid sequence of the TIC11304-His protein
                         encoded by SEQ ID NO:18.
                        organism = synthetic construct
SEQUENCE: 19
MSDSPGINIS MVAAPTPAGC SIGAVGKMVR PIQDSDVPYF FPNGVVSAMQ HHYPGYNIGG  60
AWLHDPTPGA PYSDMFAYYK DWPGGPTPVT VIYKPVSARV VSMSPEAAYK YDQDFINESS 120
VGATFNCSLT QSVTNSVSTT KTEGDSLKVG QKLTYGVEFL GSGVKGETSA EYTHTWGTSD 180
TNTTTVTVGT ASGISVFLEP GQKVTAELTA SRSKLVVEVT YDVTLDGSVV FTTPNWDLGG 240
HRDHWFWVGS LLDDANGGNP PNSSVGIRRT EQITLDFYAN GVTRLLDNTG KVLLTVEGGR 300
GQAEAKDEKS FTLEALREAA SLGAHHHHHH                                  330

SEQ ID NO: 20            moltype = AA  length = 320
FEATURE                 Location/Qualifiers
source                  1..320
                        mol_type = protein
                        organism = Arthrobacter sp.
SEQUENCE: 20
MSDSPGINIS MVAAPTQARC SVGATGKIVK QIEDSDIPYF FPNGVSSAMQ HHFPHNKIGG  60
AWLHDPTPGA PYSNMFDYYK NWQGGPSPVT VVYKPVSAKI VSLTPEDAYK YDQEFINDSS 120
VPGTFNCSLT QSVTNSVSTT KTEGDSLKVG QKFGYGVEFL GTGAKGETSA EYQHSWGTSD 180
TNMTTVTVGT STGLSVLLQP GQRVKAELSA AHSKLVVEVT YDVTLDGSVI YTFPNWDDGH 240
RDHWFWAGSL LDDANGGNPP NSSVGIRRTE QITLDYYSNG VTRLLDINGN LLLTVEDGHG 300
RGEAKDGGPL TLEELRKQLR                                            320
```